US008476510B2

(12) United States Patent
Swager et al.

(10) Patent No.: US 8,476,510 B2
(45) Date of Patent: Jul. 2, 2013

(54) COMPOSITIONS COMPRISING AND METHODS FOR FORMING FUNCTIONALIZED CARBON-BASED NANOSTRUCTURES

(75) Inventors: Timothy M. Swager, Newton, MA (US); William R. Collins, Durango, CO (US); Wiktor Lewandowski, Warsaw (PL); Ezequiel Schmois, Cambridge, MA (US); Stefanie Sydlik, Cambridge, MA (US); Joseph Walish, Cambridge, MA (US); John B. Goods, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 6 days.

(21) Appl. No.: 13/288,734

(22) Filed: Nov. 3, 2011

(65) Prior Publication Data
US 2012/0116094 A1 May 10, 2012

Related U.S. Application Data

(60) Provisional application No. 61/409,844, filed on Nov. 3, 2010.

(51) Int. Cl.
C07C 45/00 (2006.01)
(52) U.S. Cl.
USPC .......................................... 977/748; 568/319
(58) Field of Classification Search
USPC ........................................................ 977/748
See application file for complete search history.

(56) References Cited

U.S. PATENT DOCUMENTS

| | | | |
|---|---|---|---|
| 3,450,878 A | 6/1969 | Pezdirtz et al. |
| 3,915,706 A | 10/1975 | Limburg et al. |
| 4,616,237 A | 10/1986 | Pettigrew et al. |
| 5,753,088 A | 5/1998 | Olk |
| 6,616,497 B1 | 9/2003 | Choi et al. |
| 6,652,958 B2 | 11/2003 | Tobita |
| 6,705,910 B2 | 3/2004 | Sheu et al. |
| 6,902,658 B2 | 6/2005 | Talin et al. |
| 7,014,743 B2 | 3/2006 | Zhou et al. |
| 7,187,115 B2 | 3/2007 | Seon |
| 7,365,100 B2 | 4/2008 | Kuper et al. |
| 7,556,775 B2 | 7/2009 | McGill et al. |
| 7,854,826 B2 | 12/2010 | So et al. |
| 7,871,533 B1 | 1/2011 | Haiping et al. |
| 8,187,887 B2 | 5/2012 | Swager et al. |
| 8,212,132 B2 | 7/2012 | Swager et al. |
| 2002/0037457 A1 | 3/2002 | Choi |
| 2006/0057927 A1 | 3/2006 | Kang et al. |
| 2006/0063464 A1 | 3/2006 | Kang et al. |
| 2006/0202168 A1 | 9/2006 | Barrera et al. |
| 2007/0179272 A1 | 8/2007 | Tobe et al. |
| 2008/0076816 A1 | 3/2008 | Bianco et al. |
| 2008/0131658 A1 | 6/2008 | Wakharkar et al. |
| 2008/0221240 A1 | 9/2008 | Swager et al. |
| 2009/0058258 A1 | 3/2009 | Chang et al. |
| 2009/0305089 A1 | 12/2009 | Minteer et al. |
| 2010/0179054 A1 | 7/2010 | Swager et al. |
| 2010/0222432 A1 | 9/2010 | Hua |
| 2011/0081724 A1 | 4/2011 | Swager et al. |
| 2011/0089051 A1 | 4/2011 | Wang et al. |
| 2011/0171629 A1 | 7/2011 | Swager et al. |
| 2012/0171093 A1 | 7/2012 | Swager et al. |

FOREIGN PATENT DOCUMENTS

| | | |
|---|---|---|
| CN | 1995143 A | 7/2007 |
| JP | 63-221278 A | 9/1988 |
| JP | 2008-047855 A | 2/2008 |
| WO | WO 01/10779 A1 | 2/2001 |
| WO | WO 2004/113275 A2 | 12/2004 |
| WO | WO 2006/104046 A1 | 10/2006 |
| WO | WO 2006/115486 A1 | 11/2006 |
| WO | WO 2007/033189 A1 | 3/2007 |
| WO | WO 2007/098578 A1 | 9/2007 |
| WO | WO 2007/143028 A2 | 12/2007 |
| WO | WO 2008/133779 A2 | 11/2008 |
| WO | WO 2009/136978 A2 | 11/2009 |

OTHER PUBLICATIONS

Collins et al. Chemical Communication, 2011, 47, 8790-8792.*
International Preliminary Report on Patentability for PCT/US2010/051610 mailed Apr. 19, 2012.
International Preliminary Report on Patentability for PCT/US2010/055395 mailed May 18, 2012.
Georgakilas et al., Organic functionalization of carbon nanotubes. J Am Chem Soc. Feb. 6, 2002;124(5):760-1.
Kubat et al., Degradation of pyrene by UV radiation. Journal of Photochemistry and Photobiology A: Chemistry. 2000;132:33-36.
International Search Report and Written Opinion for PCT/US2010/051610 mailed Mar. 5, 2012.
International Search Report and Written Opinion for PCT/US2010/055395 mailed Mar. 20, 2012.
Raval et al., Determining ionizing radiation using sensors based on organic semiconducting material. Appl Phys Lett. 2009;94:123304-1-123304-3.
Tang et al., Measurement of ionizing radiation using carbon nanotube field effect transistor. Phys Med Biol. Feb. 7, 2005;50(3):N23-31.
Yates et al., The absorption coefficient spectrum and radiaiton degradation of poly(butene-1 sulfone) in the soft X-ray region. J Poly Sci Part B Poly Phys. 1993;31:1837-44.
International Search Report and Written Opinion for PCT/US2008/003180 mailed Jun. 19, 2009.
International Preliminary Report on Patentability for PCT/US2008/003180 mailed Sep. 17, 2009.
Invitation to Pay Additional Fees for PCT/US2009/001396 mailed Dec. 10, 2009.
International Search Report and Written Opinion for PCT/US2009/001396 mailed Apr. 22, 2010.
International Preliminary Report on Patentability for PCT/US2009/001396 mailed Sep. 16, 2010.

(Continued)

Primary Examiner — Nizal Chandrakumar
(74) Attorney, Agent, or Firm — Wolf, Greenfield & Sacks, P.C.

(57) ABSTRACT

The present invention generally relates to compositions comprising and methods for forming functionalized carbon-based nanostructures.

17 Claims, 31 Drawing Sheets

OTHER PUBLICATIONS

International Search Report and Written Opinion for PCT/US2009/006512 mailed Oct. 22, 2010.

International Preliminary Report on Patentability for PCT/US2009/006512 mailed Jun. 23, 2011.

Invitation to Pay Additional Fees for PCT/US2010/051610 mailed Dec. 27, 2011.

Invitation to Pay Additional Fees for PCT/US2010/055395 mailed Dec. 7, 2011.

[No Author Listed] TGP-H Carbon Fiber Paper. Toray Automotive Solutions. Toray Industries (America), Inc. Available at http://www.toray-auto.us/poductrs/carbon_papers_fuel_cells.html. Last accessed Nov. 19, 2010. 2 pages.

Albert et al., Cross-reactive chemical sensor arrays. Chem Rev. Jul. 12, 2000;100(7):2595-626.

Bai et al., Gas Sensors Based on Conducting Polymers. Sensors. 2007;7:267-307.

Baughman et al., Carbon Nanotubes—The Route Toward Applications. Science. 2002;297(2):787-92.

Becker et al., The Influence of Surface Strain on the Chemical Reactivity of Fullerene Ions: Addition Reactions with Cyclopentadiene and 1,3-cycolhexadiene. International Journal of Mass Spectrometry and Ion Processes. 1997;167/168:519-24.

Chen et al., Dissolution of Full-Length Single-Walled Carbon Nanotubes. J Phys Chem B. 2001;105:2525-28.

Chen et al., Noncovalent functionalization of carbon nanotubes for highly specific electronic biosensors. Proc Natl Acad Sci U S A. Apr. 29, 2003;100(9):4984-9. Epub Apr. 15, 2003.

Coffey et al., Conducting Polymer/Graphite Fiber Composites for High Charge Density Battery Electrodes. Lithium batteries—Symposium. Proceedings—Electrochemical Society. New Orleans, LA. Oct. 1993. The Society. 1994;94-4:258-68.

Coffey et al., High charge density conducting polymer/graphite fiber composite electrodes for battery applications. J Electrochem Soc. 1995;142(2):321-25.

Collins et al., Extreme oxygen sensitivity of electronic properties of carbon nanotubes. Science. Mar. 10, 2000;287(5459):1801-4.

Diederich et al., Covalent Fulleren Chemistry. Science. 1996;271:317-23.

Dwyer et al., DNA-functionalized single-walled carbon nanotubes. Nanotechnology. 2002;13(5):601-04.

Giordani et al., Multifunctional hybrid materials composed of [60]fullerene-based functionalized-single-walled carbon nanotubes. Carbon. 2009;47(3):578-88.

Guo et al., Covalently bridging gaps in single-walled carbon nanotubes with conducting molecules. Science. Jan. 20, 2006;311(5759):356-9.

Hahm et al., Direct Ultrasensitive Electrical Detection of DNA and DNA Sequence Variations Using Nanowire Nanosensors. Nano Letters. 2004; 4(1):51-54.

Janata et al., Conducting polymers in electronic chemical sensors. Nat Mater. Jan. 2003;2(1):19-24.

Jung et al., Covalent attachment and hybridization of DNA oligonucleotides on patterned single-walled carbon nanotube films. Langmuir. Sep. 28, 2004;20(20):8886-91.

Kamat et al., Self-Assembled Linear Bundles of Single Wall Carbon Nanotubes and Their Alignment and Deposition as a Film in a dc Field. J Am Chem Soc. 2004;126(34):10757-62.

Khare et al., Carbon Nanotube Based Composites—A Review. Journal of Minerals & Materials Characterization & Engineering. 2005; 4(1):31-46.

Kolmakov et al., Chemical Sensing and Catalysis by One-Deminsional Metal-Oxide Nanostructures. Annu Rev Mater Res. 2004;34:151-80.

Kong et al., Nanotube molecular wires as chemical sensors. Science. Jan. 28, 2000;287(5453):622-5.

Liu et al., Fullerene pipes. Science. May 22, 1998;280(5367):1253-6.

Lobez et al., Radiation Detection: Resistivity Responses in Functional Poly (Olefin Sulfone)/Carbon Nanotube Composites. Angew Chem Int Ed. 2010; 49:95-98.

Lutz, 1,3-Dipolar cycloadditions of azides and alkynes: a universal ligation tool in polymer and materials science. Angew Chem Int Ed. 2007; 46:1018-25.

Maggini et al., Addition of Azomethine Ylides to $C_{60}$: Synthesis, Characterization, and Functionalization of Fullerene Pyrrolidines. J Am Chem Soc. 1993;115: 9798-99.

McQuade et al., Conjugated Polymer-Based Chemical Sensors. Chem Rev. 2000;100:2537-74.

Moses et al., The growing applications of click chemistry. Chem Soc Rev. Aug. 2007;36(8):1249-62. Epub May 3, 2007.

O'Donovan et al., Phosphine-catalysed cycloaddition of buta-2,3-dienoates and but-2-ynoates to [60]fullerene. Chem Commun. 1997:81-82.

Pederson et al., Core particle, fiber, and transcriptionally active chromatin structure. Annu Rev Cell Biol. 1986;2:117-47.

Park et al., Enhancement of the field-effect mobility of poly(3-hexylthiophene)/functionalized carbon nanotube hybrid transistors. Org Electon. 2008;9:317-22.

Potyrailo, Polymeric Sensoir Materials: Toward an Alliance of Combinatorial and Rational Design Tools? Agnew Chem Int Ed. 2006;45:702-23.

Prato et al., Fulleropyrrolidines: A Family of Full-Fledged Fullerene Derivatives. Acc Chem Res. 1998;31(9):519-26.

Preda et al., Addition of Dihalocarbenes to Corannulene. A Fullerene-Type Reaction. Tetrahedron Letters. 2000;41: 9633-37.

Qi et al., Toward Large Arrays of Multiplex Functionalized Carbon Nanotube Sensors for Highly Sensitive and Selective Molecular Detection. Nano Lett. 2003;3(3):347-51.

Rostovtsev et al., A stepwise huisgen cycloaddition process: copper(I)-catalyzed regioselective "ligation" of azides and terminal alkynes. Angew Chem Int Ed Engl. Jul. 15, 2002;41(14):2596-9.

Santhanam et al., A chemical sensor for chloromethanes using a nanocomposite of multiwalled carbon nanotubes with poly(3-methylthiophene). Sensors and Actuators B. 2005;106:766-71.

Scott, Fragments of Fullerenes: Novel Syntheses, Structures and Reactions. Pure & Appl Chem., 1996;68(2):291-300.

Serp et al., Carbon Nanotubes and Nanofibers in Catalysis. Applied Catalysis A: General. 2003;253:337-58.

Shu et al., Phosphine-catalysed [3+2] cycloadditions of buta-2,3-dienoates with [60]fullerene. Chem Commun. 1997;79-80.

Silverman, The Organic Chemistry of Drug Design and Drug Action. 2nd ed. 2004;29-32.

Snow et al., Chemical detection with a single-walled carbon nanotube capacitor. Science. Mar. 25, 2005;307(5717):1942-5.

Star et al., Electronic Detection of Specific Protein Binding Using Nanotube FET Devices. Nano Lett. 2003;3(4):459-63.

Star et al., Nanoelectronic Carbon Dioxide Sensors. Adv Mater. 2004;16(22):2049-52.

Sun et al., Functionalized Carbon Nanotubes: Properties and Applications. Acc Chem Res. 2002;35(12):1096-1104.

Swager, The Molecular Wire Approach to Sensory Signal Amplificiation. Acc Chem Res. 1998;31:201-07.

Tasis et al., Chemistry of Nanotubes. *Chem Rev.* 2006;106:1105-36.

Toal et al., Polymer sensors for niroaromatic explosives detection. Mater Chem. 2006;16:2871-83.

Tombler et al., Reversible electromechanical characteristics of carbon nanotubes under local-probe manipulation. Nature. 2000;405:769-72.

Wang et al., Carbon Nanotube/Polythiophene Chemiresistive Sensors for Chemical Warfare Agents. J Am Chem Soc. 2008;130:5392-93.

Wang et al., Novel multicomponent reaction of [60]fullerene: the first example of 1,4-dipolar cycloaddition reaction in fullerene chemistry. Org Biomol Chem. 2006;4:4063-64.

Wei et al., Covalent functionalization of single walled carbon nanotubes and fullerences via a switterion approach. Chemical Abstracts. 2007. 2 pages.

Wei et al., Multifunctional chemical vapor sensors of aligned carbon nanotube and polymer composites. J Am Chem Soc. Feb. 8, 2006;128(5):1412-3.

Weizmann et al., DNA-CNT nanowire networks for DNA detection. J Am Chem Soc. Mar. 16, 2011;133(10):3238-41. Epub Feb. 22, 2011.

Zaharescu et al., Electrical properties of polyolefin blends under γ-radiation exposure. ICSD 2004. Proceedings of the 2004 Inter National Conference on Solid Dielectrics. Toulouse, France. Jul. 5-9, 2004. IEEE. Jul. 5, 2004;1:367-69.

Zhang et al., Covalent Functionalization of Singled Walled Carbon Nanotubes and Fullerenes via a Zwitterion Approach. Prep Pap.-Am Chem Soc, Div Fuel Chem.. 2007;52(1):126-28.

Zhang et al., Electrochemically Functionalized Single-Walled Carbon Nanotube Gas Sensor. Electroanalysis. 2006;18(12):1153-58.

Zhang et al., Functionalization of single-walled carbon nanotubes and fullerenes via a dimethyl acetylenedicarboxylate-4-dimethylaminopyridine zwitterion approach. J Am Chem Soc. Jun. 27, 2007;129(25):7714-5. Epub Jun. 2, 2007.

Zhang et al., Modular Functionalization of Carbon Nanotubes and Fullerenes. J Am Chem Soc. 2009;131:8446-54.

Zhou et al., A New Method for the Functionalization of [60] Fullerene: An Unusual 1,3-Dipolar Cycloaddition Pathway Leading to a $C_{60}$ Housane Derivative. Organic Letters. 2005;7(26):5849-51.

* cited by examiner

| Atomic Wt% | Solvent | Temp | % (C) | % (O) | % (N) |
|---|---|---|---|---|---|
|  | THF | 66 | 78.95 | 19.65 | 1.40 |
|  | Dioxane | 100 | 85.47 | 12.40 | 2.13 |
|  | Diglyme | 150 | 85.81 | 11.29 | 3.19 |
| GO | -- | -- | 72.3 | 27.7 | -- |
| Functional Groups: |  |  | Graphene C | Graphene O | Amide Groups |
|  | THF | 66 | 52 | 13 | 1 |
|  | Dioxane | 100 | 36 | 5 | 1 |
|  | Diglyme | 150 | 22 | 3 | 1 |

Fig. 11G

Fig. 12A
| Atomic Wt% | Time | % (C) | % (O) | % (N) |
|---|---|---|---|---|
| SM | — | 85.81 | 11.29 | 3.19 |
|  | 36 h | 82.42 | 16.51 | 1.06 |
Fig. 12B
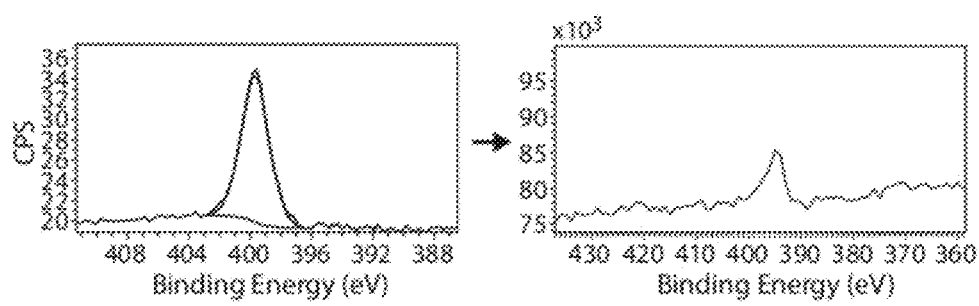
Fig. 12C

| Sample | Zeta Potential [mV] | Sample | Conductivity [S/m] |
|---|---|---|---|
| GO | -19.5 | GO | Insulator |
| Carboxylic Acid | -34.1 | Carboxylic Acid | 3.74 |
| Potassium Salt Carboxylate | -58.6 | Carboxylic Acid (Annealed 250 °C) | 138.2 |

All samples: 1 mg/mL

1: Covalently Functionalized Graphene

2: Physioadsorbed Ketone + Reduced GO

3: Reduced GO

COMPOSITIONS COMPRISING AND METHODS FOR FORMING FUNCTIONALIZED CARBON-BASED NANOSTRUCTURES

RELATED APPLICATIONS

This application claims priority under 35 U.S.C. §119(e) to U.S. Provisional Patent Application No. 61/409,844, filed Nov. 3, 2010, and entitled "Compositions Comprising and Methods for Forming Functionalized Carbon-Based Nanostructures" which is incorporated herein by reference in its entirety for all purposes.

GOVERNMENT SUPPORT

This invention was made with government support under Grant No. HM1582-09-1-0025 awarded by the National Geospatial Intelligence Agency. The government has certain rights in this invention.

FIELD OF THE INVENTION

The present invention generally relates to compositions comprising and methods for forming or using functionalized carbon-based nanostructures.

BACKGROUND OF THE INVENTION

Carbon-based nanostructures, including two-dimensional graphene nanosheets and graphene-based materials, have garnered an increasingly large amount of scientific interest in recent years due to their structural and electronic properties. Conventional methods for synthesizing graphene-based materials utilize graphite oxide (GO) as a starting material, which can be prepared in bulk quantities from commercial-grade graphite under strong oxidizing conditions. GO in its bulk form is a layered material composed of a variety of oxygen-containing functionalities, for example, epoxides and tertiary alcohol groups are generally found on the basal plane and carbonyl and carboxyl groups along the sheet edges. The diversity and density of functionality in GO provides a platform for chemistry to occur both within the inter-sheet gallery and along sheet edges.

Despite the recent upsurge in methods for forming graphene derivatives along with subsequent incorporation of the products into graphene-based devices, only a few methods exist to covalently functionalize the basal plane of graphene. Moreover, current methodology often introduces basal plane functionalities that are weakly bound to the graphene surface through carbon-oxygen (C—O) or carbon-nitrogen (C—N) bonds and therefore, the resulting material generally cannot survive further thermal, electrochemical, and/or chemical treatment of the graphene-based material. The labile nature of such chemical functionalities represents a significant drawback to the currently available technology, as in many cases it is necessary to deoxygenate the graphene derivatives under relatively harsh conditions to reestablish electrical conductivity within the graphene nanosheet. Additionally, incorporation of these C—O or C—N modified graphene materials into devices can intrinsically limit the thermal and/or electrochemical boundaries of the device.

SUMMARY OF THE INVENTION

In some aspects of the present invention, compositions are provided. In some embodiments, a composition comprises graphene or graphene oxide comprising at least one functional group associated with the graphene or graphene oxide, wherein the at least one functional group has the structure:

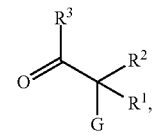

wherein $R^1$, $R^2$, and $R^3$ are the same or different and each is independently a substituent, optionally substituted; and G comprises a carbon atom of the graphene or graphene oxide In other aspects of the present invention, methods are provided. In some embodiments, a method for fabricating a functionalized carbon-based nanostructure comprises providing a carbon-based nanostructure comprising an allylic functional group, reacting the carbon-based nanostructure with a reactant comprising at least one carbon atom, and causing a carbon-carbon bond to form between the at least one carbon atom within the reactant and a carbon atom within the carbon-based nanostructure. In another embodiment, a method for fabricating a functionalized carbon-based nanostructure comprises providing a carbon-based nanostructure including a group having the formula (I):

wherein $C^1$, $C^2$, and $C^3$ are part of a fused network of aromatic rings within the carbon-based nanostructure and $OR^5$ is a pendant group of the fused network of aromatic rings, wherein $R^5$ is a substituent, optionally substituted, and reacting the carbon-based nanostructure with a reactant to produce a group having formula (II):

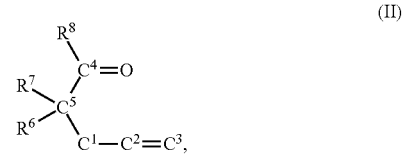

wherein $R^6$, $R^7$, and $R^8$ are the same or different and each is independently a substituent, optionally substituted.

In some embodiments, a device comprising a composition as described herein and/or a composition formed using a method as described herein are provided. In another aspect, the present invention encompasses methods of making one or more of the embodiments described herein. In still another aspect, the present invention encompasses methods of using one or more of the embodiments described herein.

In some embodiments, a method for reducing the amount of an species in a sample is provided. In some cases, the method comprises contacting a vapor phase sample containing a first concentration of the species with a composition comprising substituted graphene or graphene oxide molecules such that the vapor phase sample has a second, decreased concentration of the species after contact with the composition.

In some embodiments, the method comprises contacting a sample containing a first concentration of the species with a composition comprising graphene or graphene oxide, wherein the graphene or graphene oxide comprises at least one functional group having the structure:

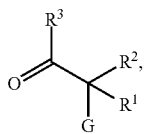

wherein $R^1$, $R^2$, and $R^3$ are the same or different and each is a substituent, optionally substituted; and G comprises a carbon atom of the graphene or graphene oxide, such that the sample has a second, decreased concentration of species after contact with the composition.

In some embodiments, a catalyst composition is provided. In some cases, the catalyst composition comprises a graphene or graphene oxide molecule comprising at least one functional group having the structure:

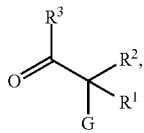

wherein:

$R^1$, $R^2$, and $R^3$ are the same or different and each is independently a substituent, optionally substituted, wherein at least one of $R^1$, $R^2$, and $R^3$ comprises a catalytic moiety capable of oxidizing carbon monoxide to carbon dioxide; and G comprises a carbon atom of the graphene or graphene oxide.

In some embodiments, the method comprises contacting a sample comprising carbon monoxide with a graphene or graphene oxide molecule comprising at least one functional group having the structure:

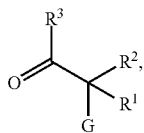

wherein:

$R^1$, $R^2$, and $R^3$ are the same or different and each is independently hydrogen or a substituent, optionally substituted; and G comprises a carbon atom of the graphene or graphene oxide.

BRIEF DESCRIPTION OF THE DRAWINGS

FIG. 12 shows (a) the saponification of an allylic ester-functionalized graphene oxide; (b) XPS data and (c) XPS plot for a carboxylic acid-functionalized graphene oxide.

Figure 1:
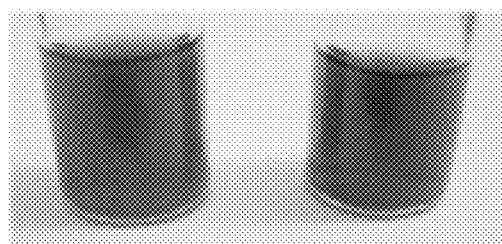
FIG. 1 shows non-limiting images of a reaction of the present invention, according to some embodiments.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention generally relates to compositions comprising functionalized carbon-based nanostructures such as functionalized graphene nanosheets, and related methods. Functionalized graphene-based materials and other carbon-based nanostructures may find use in many applications, such as those described herein. Some embodiments of the invention enhance the processability and/or solubility of carbon-based nanostructures (e.g., graphene and graphene-based materials), for example, for use with such applications.

In some embodiments, the present invention provides methods which allow for relatively large-scale production of functionalized graphene (e.g., graphene nanosheets) using graphene oxide as the bulk starting material. Graphene oxide will be known to those of ordinary skill in the art and generally refers to an oxygenated form of the common carbon allotrope graphene, and is readily available and generally inexpensive. The methods described herein not only allow for chemically functionalizing the graphene oxide, but also may allow for subsequent deoxygenation of the graphene oxide following functionalization, e.g., without causing disassociation or decomposition of the chemical functionalities. For example, a two-step procedure can be utilized according to certain embodiments, comprising 1) oxidation with concomitant exfoliation to graphene oxide, and 2) chemical, electrochemical, or thermal reduction to reestablish molecular conjugation and conductivity of the graphene oxide.

In some cases, the method comprises functionalizing graphene oxide with a plurality of functional groups, wherein each functional group is associated with (e.g., attached to) the graphene network via a carbon-carbon bond. The carbon-carbon bond formed during functionalization may be capable of withstanding conditions necessary for further functionalizing the graphene and/or the functional groups, and/or reduction of the graphene. In some cases, the methods utilize relatively non-toxic and/or essentially non-toxic materials as compared to currently known methods.

In some embodiments, the compositions and methods described herein provide carbon-based nanostructures, such as graphene oxide or graphene, comprising functional groups associated with the carbon-based nanostructure, generally via a carbon-carbon bond, wherein the functional group comprise a carbonyl group (e.g., ester, carboxylic acid, carboxylate, aldehyde, amide, ketone, any of which is optionally substituted). In some cases, the carbonyl group is an allylic carbonyl group. The carbonyl groups may be further functionalized and may provide access to materials useful in a variety of applications. For example, the carbonyl groups may bind metal ions, and may find use as molecular scaffolds for metal nanoparticles (e.g., for catalytic processes, for chemosensing) or to trap metal ions. In some cases, the compositions can be used as an n-type material (e.g., electron transport semiconductor) for various applications including quantum-dot based photovoltaic cells. In other cases, the compositions may be used as an anode and/or cathode material, e.g., to bind lithium ions in lithium ion batteries, in graphene-nanoparticle hybrid batteries. Additionally, the carbonyl groups may be themselves functionalized, thereby allowing for additional tuning of the structural and/or electronic properties of the composition. For example, amide functionalized materials may display expanded intersheet distances (e.g., in comparison to graphite and chemically reduced graphene) and/or high surface areas, and may find application as supercapacitors. Additional applications and uses and well as functionalization of the carbonyl groups are described herein.

The methods and/or compositions described herein provide numerous advantages and/or improvements over current methods and/or compositions. For example, while known methods for functionalizing graphene with carbon-carbon bonds generally utilize either unstable colloidal solutions of preformed graphene nanosheets (e.g., arylation methods) or air and/or water sensitive metal-intercalated graphite (e.g., alkylation methods), the methods described herein generally utilize air and water (bench-stable) graphite oxide (GO) as the starting material for the chemical transformation. The methods and/or compositions also may comprise high functional group densities, as described herein, which are generally higher than known methods/compositions. In addition, the methods described herein can be conducted on large scales (e.g., kilotons of product). Furthermore, many of the methods and systems discussed herein are applicable not only to graphene oxide, but to other carbon-based nanomaterials as well, for example, carbon nanotubes (single or multi-walled), fullerenes, or the like. Further examples of carbon-based nanomaterials are described in detail below.

In some embodiments of the present invention, compositions are provided. In some cases, the composition comprises graphene or graphene oxide associated with at least one functional group. A functional group may be bound to (e.g., attached to) the graphene network via a carbon-carbon bond (e.g., a carbon-carbon single bond), where one of the carbon atoms forming the carbon-carbon bond is not itself part of the mesh or fused network of carbon atoms that defines the graphene network itself. Typically, the carbon atoms defining the graphene or graphene oxide network are arranged in a two-dimensional hexagonal or "honeycomb" structure. In some cases, the functional group bound to the graphene network comprises a carbonyl group.

In some embodiments, the at least one functional group associated with graphene or graphene oxide has the structure:

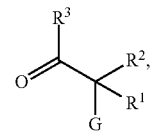

wherein $R^1$, $R^2$, and $R^3$ can be the same or different, and each is individually hydrogen or another suitable substituent, optionally substituted, and G comprises a carbon atom of the graphene or graphene oxide. In some embodiments, G comprises a carbon atom positioned within the basal plane of the graphene or graphene oxide (e.g., G is an interior carbon atom of the fused network of graphene or graphene oxide). The term "substituent" as used herein will be understood by those of ordinary skill in the art and refers to all permissible substituents of the structure being referred to, "permissible" being in the context of the chemical rules of valence known to those of ordinary skill in the art. In some cases, the suitable substituent may be a salt. The suitable substituent may be an organic substituent or non-organic substituent.

In some cases, $R^1$ and $R^2$ can be the same or different and each are independently hydrogen, alkyl, heteroalkyl, cycloalkyl, alkenyl, or aryl, any of which is optionally substituted. In some embodiments, $R^1$ and $R^2$ are both hydrogen. In some cases, $R^3$ is hydrogen, alkyl, aryl, alkenyl, cycloalkyl, heteroalkyl, heteroaryl, $N(R^4)_2$, $SR^4$, $Si(R^4)_2$, $OR^4$, or OM, any of which is optionally substituted, wherein M is a metal or cationic species and $R^4$ is a suitable substituent (e.g., hydrogen, an organic substituent, a metal-containing substituent), optionally substituted. In some cases, each $R^4$ can be the same or different and are hydrogen, alkyl, cycloalkyl, haloalkyl, heteroalkyl, aryl, heteroaryl, or OH, any of which is optionally substituted. In some cases, at least one of $R^1$, $R^2$, or $R^3$ is haloalkyl. In a particular embodiment, $R^3$ is $OR^4$ or $N(R^4)_2$. In some embodiments, $R^4$ is alkyl substituted with an unsubstituted or substituted aryl or an unsubstituted or substituted cycloalkyl.

In some cases, $R^3$ is $N(CH_3)_2$, NH-phenyl, NH-biphenyl, $NHCH_2(C{\equiv}CH)$, OH, OMe, OEt, OM, where M is a metal ion, $OCH_2(C{\equiv}CH)$, $OCH_2CH_2$(2-bromophenyl), $OCH_2$(adamantyl), or $OCH_2C$(4-chlorophenyl)$_3$.

In one set of embodiments, $R^1$ and $R^2$ are both hydrogen; and $R^3$ is OH.

In one set of embodiments, $R^1$ and $R^2$ are both hydrogen; and $R^3$ is OMe or OEt.

In some embodiments, the compositions and methods described herein comprise carbon-based nanostructures (e.g., graphene oxide and/or graphene) having a high density of functional groups. As used herein, a carbon-based nanostructure having a "high density of functional groups" refers to carbon-based nanostructures comprising a plurality of functional groups attached to the surface of the nanostructure, wherein the ratio of number of functional groups to number of carbon atoms of the surface of the nanostructure is at least about 1 to 50. The ratio may also be considered in some embodiments as the surface density of functional groups on the surface of the nanostructure for a given unit area of the nanostructure, as defined by the number of carbon atoms within that given unit area. In some cases, the ratio of functional groups to carbon atoms of the surface of the nanostructure is at least about 1 to 25, at least about 1 to 20, at least about 1 to 15, at least 1 to 10, at least about 1 to 9, at least about 1 to 8, at least about 1 to 7, at least about 1 to 6, at least about 1 to 5, at least about 2 to 5, or, in some cases, at least about 1 to 4. Those of ordinary skill in the art will be aware of methods and systems for determining the ratio of functional groups to carbon atoms of the surface of the nanostructure.

In some embodiments, methods are provided for forming functionalized carbon-based nanostructures (e.g., functionalized graphenes or functionalized graphene oxides). In some cases, the functionalized carbon-based nanostructure is formed utilizing graphene oxide as a starting material. Graphene oxide may be chemically converted to a highly functionalized form of graphene or graphene oxide, in which at least a portion of the carbon-oxygen chemical bonds of the graphene oxide are transformed into carbon-carbon bonds. In some cases, an allylic alcohol functional group (e.g., a hydroxyl group with an adjacent olefinic double bond two carbon atoms away) commonly found on a graphene oxide surface is converted into an allylic carbon-carbon bond. In some cases, the allylic functional group alcohol is converted into an allylic carbon-carbon bond via an intermediary functional group, for example, an allylic vinyl ether, an allylic ester, an allylic amide, an allylic ketone, an allylic ketene acetal, an allylic N,O-ketene acetal, a beta-keto allylic ester, an allylic silyl ketene acetal, an allylic lithium enolate, an allylic sodium enolate, an allylic zinc enolate, or an allylic glycolates. The intermediary allylic functional groups can undergo a rearrangement (e.g., a sigmatropic rearrangement), in which the carbon-oxygen bond is broken, the carbon-carbon allylic double bond shifts over one bond, and a new carbon-carbon single bond is formed on the graphitic surface. A variety of pendant functional groups may be generated associated with the graphene or graphene oxide via a carbon-carbon (e.g., single) bond depending on the reaction conditions and the reagents employed. For example, graphene may be functionalized with moieties including aldehydes, carboxylic acids, esters, amides, and ketones.

The methods described herein may involve treating the graphene or graphene oxide with a reducing agent. For example, following functionalization, any remaining unreacted oxygen functionalities on the graphene or graphene oxide (e.g., unreacted allylic OH groups, etc.) may be chemically reduced, for example, using reductants such as sodium borohydride, lithium aluminum hydride, hydrazine, vitamin C (1-acsorbic acid), potassium hydroxide, thermal annealing, or ammonia. In some embodiments, the carbon-carbon bonds formed during the chemical attachment of the at least one functional group to the graphene may remain intact during and following the reduction conditions. In some cases, the resulting structure after chemical reduction is a highly reduced graphene or graphene oxide that is surface functionalized with a plurality of functional groups attached via carbon-carbon bond linkages.

Various other chemical manipulations may also optionally be performed. For example, alcohols such as primary alcohols (e.g., present as unreacted oxygen functionalities on the reduced graphene surface as described above or comprised in a functional group) may be reacted with a variety of electrophilic reagents. Alkylation and acylation of the alcohol groups may be performed in some embodiments, for example, via reaction of the modified reduced graphene with alkyl halides and acyl halides, respectively. Alkylation with perfluorinated alkyl halides may be performed, in other embodiments. The pendant alcohol groups may also readily react with epoxides to form beta-hydroxy ethers.

In some embodiments, the method comprises providing a carbon-based nanostructure comprising an allylic functional group (e.g., as may be present in graphene or graphene oxide). The carbon-based nanostructure may be reacted with a reactant comprising at least one carbon atom to form a carbon-carbon bond between the at least one carbon atom within the reactant and a carbon atom within the carbon-based nanostructure. The term "allylic functional group," as used herein in connection with a carbon-based nanostructure, refers to an allylic group which is a portion of the carbon-based nanostructure. Those of ordinary skill in the art will understand the term allylic functional group as referring to a hydroxyl group or an OR group (R being a suitable substituent, including, but not limited to, alkyl, heteroalkyl, aryl, heteroaryl, etc., optionally substituted) with an adjacent olefinic double bond two carbon atoms away, for example, having structures such as:

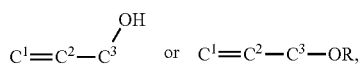

wherein $C^1$, $C^2$, and $C^3$ are part of the carbon-based nanostructure (e.g., the graphene carbon network). In some embodiments, the allylic functional group is positioned within the interior of the basal plane of the graphene or graphene oxide (e.g., not positioned at the edge or perimeter of the graphene or graphene oxide).

In some cases, the reacting step comprises reacting the carbon-based nanostructure with a reactant comprising at least one carbon atom, and transforming the allylic functional group into a second allylic functional group. That is, in some cases, the allylic group is associated with a first functional group (e.g., OR) and converted to a second allylic group comprising a second functional group (e.g., $OC(R')_2C(R'')_3$). The second allylic group may undergo rearrangement, thereby forming a carbon-carbon bond between the at least one carbon atom within the reactant and a carbon atom within the carbon-based nanostructure (e.g., the first functional group may be associated with $C^3$ of the allylic group, and the carbon-carbon bond may form between a carbon atom of the second functional group and $C^1$).

In some embodiments, the reactant is $CH_3C(OCH_3)_3$. In some embodiments, the reactant is an allylic ketene.

In some cases, a method for fabricating a functionalized carbon-based nanostructure (e.g., graphene) comprises providing a carbon-based nanostructure including a group having formula (I):

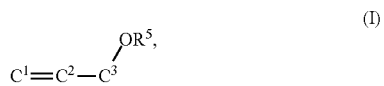

wherein $C^1$, $C^2$, and $C^3$ are part of a fused network of aromatic rings within the carbon-based nanostructure and $OR^5$ is a pendant group of the fused network of aromatic rings, wherein $R^5$ is hydrogen or another suitable substituent, optionally substituted. In some embodiments, $R^5$ is hydrogen, metal, alkyl, aryl, heteroalkyl, cycloalkyl, or oxygen-protection group, any of which is optionally substituted. In particular embodiments, $R^5$ is hydrogen. The carbon-based nanostructure may be reacted with a reactant to produce a group having formula (II):

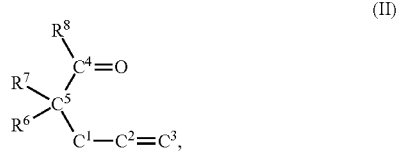

wherein $R^6$, $R^7$, and $R^8$ can be the same or different, and each is independently selected from hydrogen or another suitable substituent, optionally substituted. In some cases, $R^6$ and $R^7$ can be the same or different and each are independently hydrogen, alkyl, heteroalkyl, cycloalkyl, alkenyl, aryl, any of which is optionally substituted. In some cases, $R^8$ is hydrogen, alkyl, aryl, alkenyl, cycloalkyl, heteroalkyl, heteroaryl, $N(R^4)_2$, $SR^4$, $Si(R^4)_2$, $OR^4$, or OM, any of which is optionally substituted, wherein M is a metal or cationic species and $R^4$ is hydrogen or another suitable substituent, optionally substituted. In a particular embodiment, $R^8$ is $OR^4$ or $N(R^4)_2$. In some cases, each $R^4$ can be the same or different and are hydrogen, alkyl, cycloalkyl, haloalkyl, heteroalkyl, heteroaryl, aryl, or OH, any of which is optionally substituted.

In some embodiments, the formation of a compound of formula (II) from a compound of formula (I) (e.g., an allylic transposition) involves a rearrangement reaction. For example, the allylic transposition may be a sigmatropic rearrangement (e.g., a Claisen type rearrangement), a nucleophilic substitution reaction, or a metal catalyzed reaction. Those of ordinary skill in the art will be aware of suitable reagents and reaction conditions (e.g., solvent conditions, temperature conditions, etc.) for carrying out a rearrangement reaction, in accordance with the invention.

In some embodiments, the rearrangement is a traditional Claisen rearrangement (e.g., wherein the reagent is phenyl vinyl sulfoxide, ammonium betaines (e.g. 3-(trimethylammonio)acrylate)). In some cases, the rearrangement is an Ireland Claisen (e.g., wherein the reagents may include acyl chloride, propanoyl chloride, and lithium hexamethyldisilazide (e.g., a base)). In some cases, the rearrangement is a Johnson Claisen rearrangement (e.g., wherein the reagent may be triethylorthoformate, trimethylorthoformate, propionic acid (e.g., an acid source)). In some cases, the rearrangement may be an Eschenmoser Claisen rearrangement, (e.g., wherein the reagent is dimethylacetamide dimethylacetal).

Figure 15A:
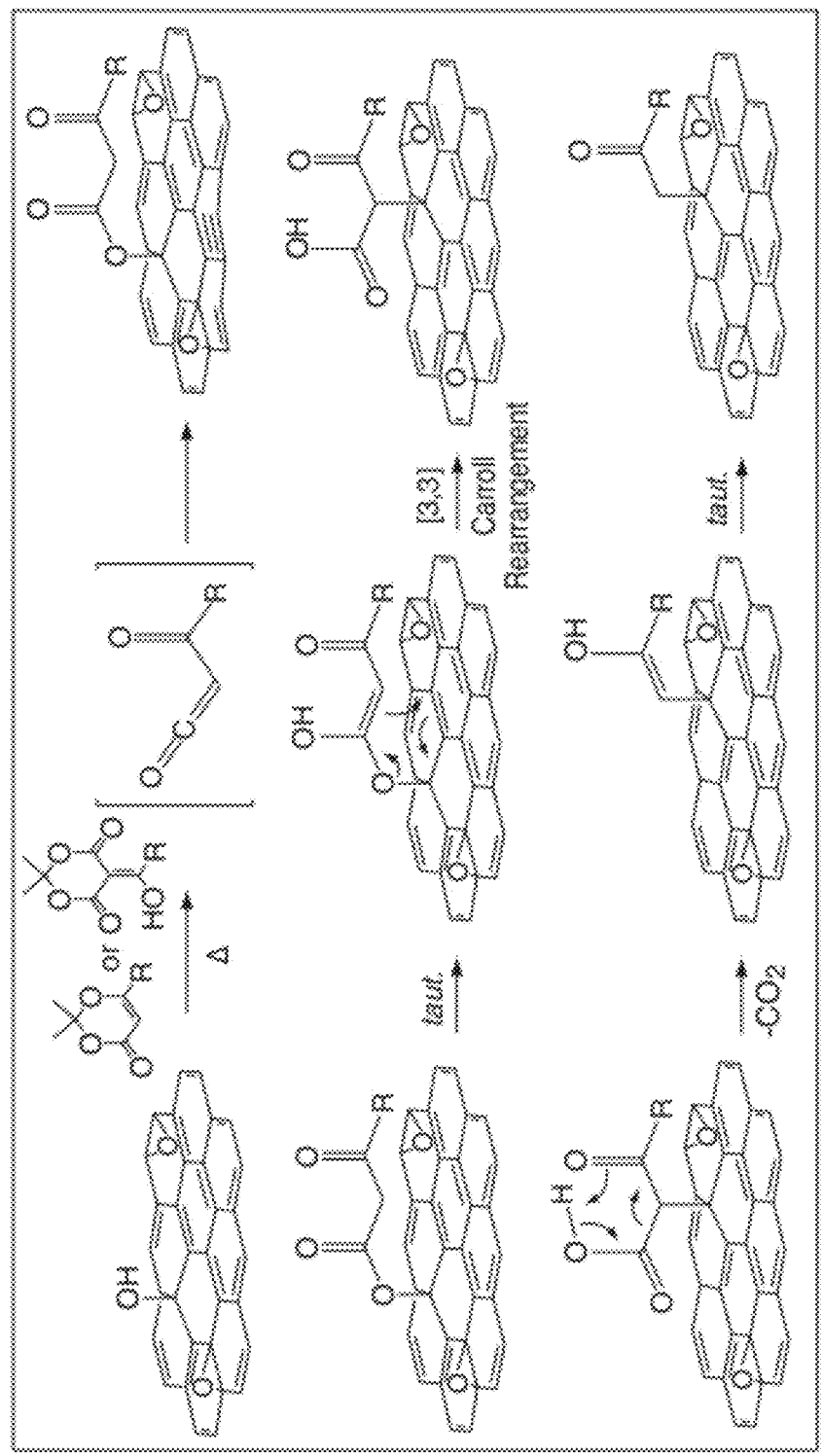
FIG. 15 shows (a) the synthesis of functionalized graphene oxides via a Carroll rearrangement; (b) illustrative reaction conditions for synthesizing functionalized graphene oxides via a Carroll rearrangement; (c) formation of an acyl ketene according to one embodiment; (d) formation of an acyl ketene according to another embodiment; (e) illustrative embodiments for synthesis of functionalized graphene oxides.
Figure 15B:
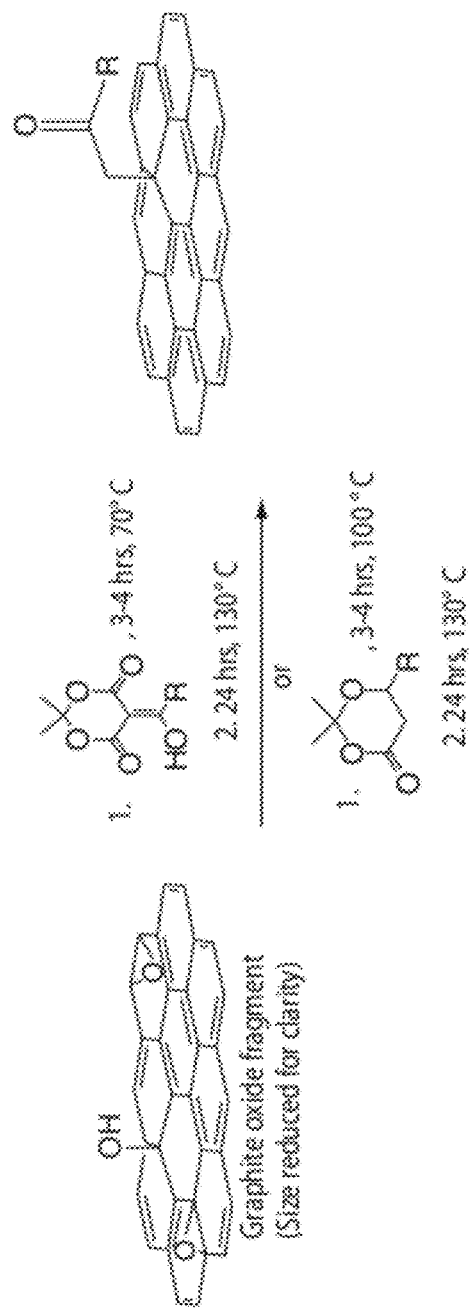
Figure 15C:
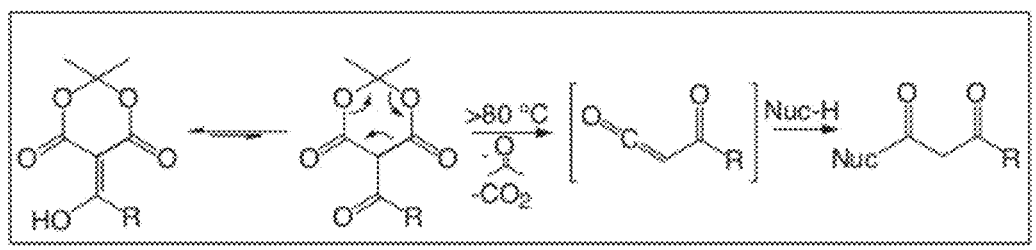
Figure 15D:
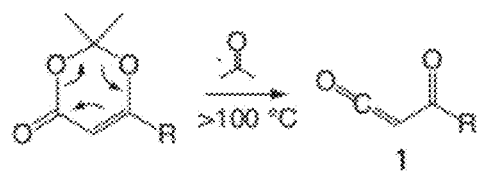
Figure 15E:
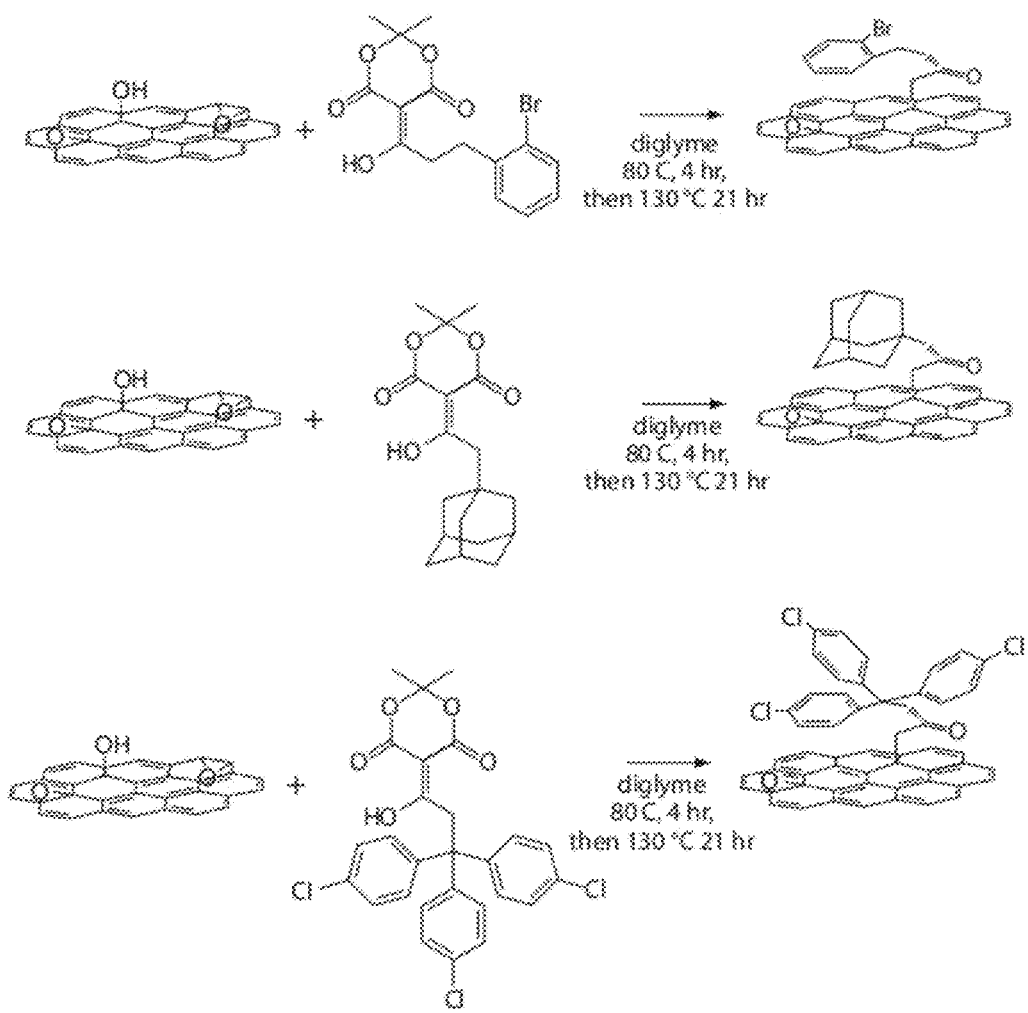

In other cases, the rearrangement may be a Carroll Claisen reaction (e.g., wherein the reagent is ethylacetoacetate), also referred to as a "Carroll reaction," "Carroll rearrangement," or "decarboxylative allylation." The Carroll rearrangement occurs when a β-keto allyl ester undergoes a [3,3] sigmatropic rearrangement to generate $CO_2$ and an allyl ketone. Typically, the β-keto allyl ester is heated, treated with base, or exposed to catalytic amounts of palladium. In some embodiments, graphene or graphene oxides functionalized with β-keto allyl esters may be generated by reaction of graphene or graphene oxide with an acyl ketene, a high energy intermediate. In an illustrative embodiment, FIG. 15A shows the reaction of graphene oxide with an acyl ketene to generate a β-keto allyl ester. Acyl ketenes can be generated using various methods known in the art, as shown in FIGS. 15B-D. One example is thermal fragmentation of acylated Meldrum's acid derivatives, Another example involves coupling of Meldrum's acid with an carboxylic acid by way of a peptide coupling reagent such as N,N'-dicyclohexylcarbodiimide or diethyl cyanophosphate. Additionally, acyl ketenes can be thermally generated from dioxinone derivatives, as shown in FIG. 15C. In some cases, the surface of graphene or graphene oxide may be exposed to a β-keto acid chloride and a non-nucleophilic base.

In some cases, reacting the carbon-based nanostructure with a reactant causes a group having formula (I) to be converted to a group having formula (III):

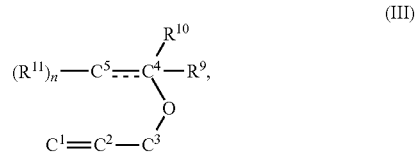

wherein $R^9$, $R^{10}$, and $R^{11}$ can be the same or different, and each is independently selected from hydrogen or another suitable substituent, optionally substituted, or wherein $R^9$ and $R^{10}$ are joined together to form =$NR^{14}$ or =O, and $R^{14}$ is hydrogen or another suitable substituent, optionally substituted, n is 2 or 3, and ═ represents a single or double bond. The group having formula (III) may then be converted to a group having formula (II), for example, via a sigmatropic rearrangement. Generally, when the compound of formula (III) is rearranged to form a compound of formula (II), $R^8$ is $R^9$ or $R^{10}$, or a salt or protonated version thereof, and $R^7$ and $R^6$ is an $R^{11}$ or a salt or protonated version thereof.

In some cases, each $R^{11}$ can be the same or different and are hydrogen, alkyl, cycloalkyl, haloalkyl, heteroalkyl, alkenyl, aryl, heteroaryl, —OH, $OR^4$ or —C(=O)$R^4$ any of which is optionally substituted, wherein $R^4$ is hydrogen or another suitable substituent, optionally substituted or as defined herein. In some cases, $R^9$, $R^{10}$, and $R^{14}$ are each independently hydrogen, alkyl, aryl, alkenyl, cycloalkyl, heteroalkyl, heteroaryl, $N(R^4)_2$, $SR^4$, $Si(R^4)_2$, $OR^4$, or OM, any of which is optionally substituted, wherein M is a metal (e.g., Na, Zn, K, Li, Ba, Ca) or cationic species and each $R^4$ can be hydrogen or another suitable substituent, optionally substituted, or as defined herein.

In some cases, the compound of formula (III) comprising one of the following structures:

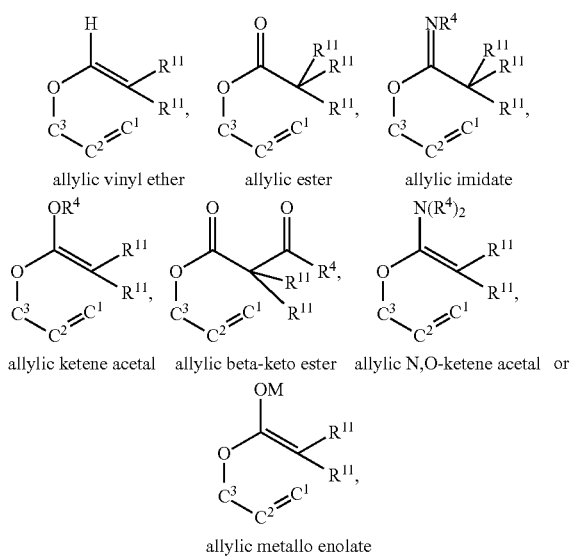

allylic vinyl ether   allylic ester   allylic imidate allylic ketene acetal   allylic beta-keto ester   allylic N,O-ketene acetal   or allylic metallo enolate wherein $C^1$, $C^2$, and $C^3$ are part of the carbon-based nanostructure, and $R^{11}$, $R^4$, and M are as defined herein. If more than one $R^{11}$ is present in a structure, the two $R^{11}$ moieties may be the same or different. In some cases, $R^4$ is silicon, alkyl, heteroalkyl, alkenyl, or aryl, optionally substituted. Those of ordinary skill in the art will be aware of suitable reagents for forming a compound of formula (III).

Figure 14A:
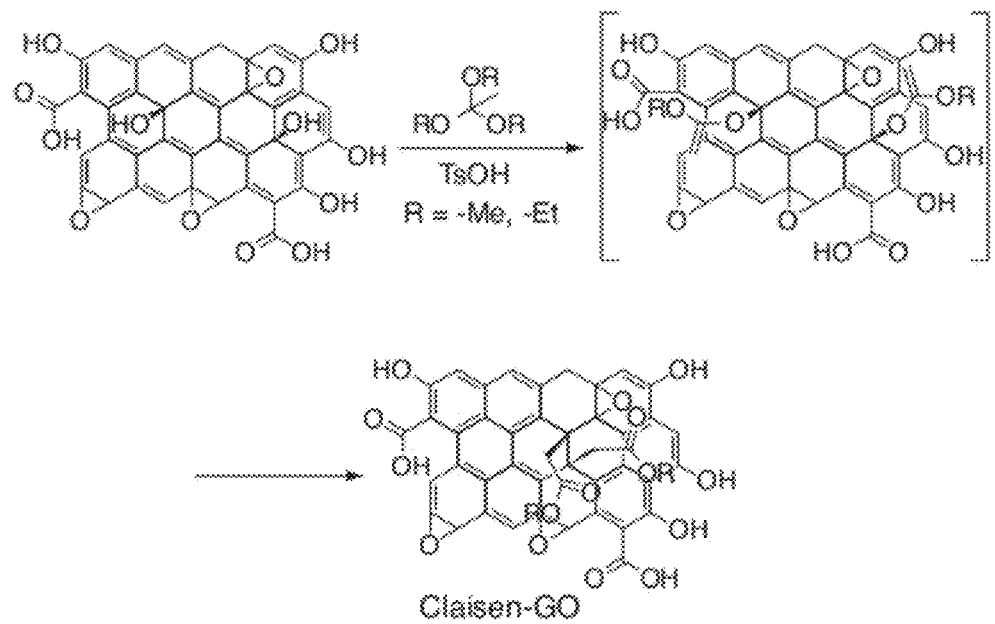
FIG. 14 shows (a) the synthesis of allyl allylic ester-functionalized graphene oxide via a Johnson-Claisen rearrangement; (b) saponification of an allyl allylic ester-functionalized graphene oxide; (c) transamidation of an allyl allylic ester-functionalized graphene oxide; (d) synthesis of graphene oxides with functional group containing an alkyne for "click" chemistry reactions; (e) an FTIR spectrum of graphene oxide substituted with
—$CH_2(C=O)NHCH_2C\equiv CH$; (f) FTIR spectra for various substituted graphene oxides; and (g) XRD plots for various substituted graphene oxides.

In some embodiments, graphene oxide may be reacted with $CH_3C(OCH_3)_3$ to produce a vinyl-ether intermediate that rearranges to produce the an allylic ester, as shown in FIG. 14A.

In some embodiments, graphene oxide may be reacted with an acyl ketene (e.g., O=C=C—(C=O)—R) to form a beta-keto-allyl ester, which can then rearrange to form an allylic ketone, as shown in FIG. 15A.

Compositions described herein may find use in various applications. In addition, the association of a carbonyl group with a carbon-based nanostructure via a carbon-carbon bond may allow access to further functionalize the carbon-based nanostructure, thus allowing for the tuning of the mechanical and/or structural properties of the carbon-based nanostructures. In some cases, the spacings between graphene sheets may be affected, at least in part, by the size, shape, chemical composition, and/or chemical affinity of the functional groups. For example, in some embodiments, if graphene oxide is used, the spacing between graphene layers can be tailored based on the type of functionalization and substituents associated with the functional group. For example, larger groups associated with the graphene (e.g., $R^6$-$R^8$ in compound of formula (II)) may create larger interlayer spacings. Additional components could be contained within the interlayer spaces and may provide functions such as charge storage and/or ion conduction. As a specific example, graphite oxide (i.e., graphene oxide sheets) has interlayer spacings of about 8.4 Å, whereas graphene functionalized with $CH_2C$(=O)$NMe_2$ groups has interlayer spacings of about 9.3 Å.

The ability to incorporate components between interlayer spaces may be useful for energy storage applications such as batteries, capacitors, etc. In some cases, the composition may be used as cathodes and/or anodes materials in batteries, or as a material in capacitors. Thus, in some embodiments, the spacing between carbon-based nanostructures (e.g., graphene sheets) can be controlled by and/or tailored though the size, shape, chemical composition, and/or chemical affinity of the functional groups associated with the carbon-based nanostructure. In some embodiments, the functional groups may increase the ability of the carbon-based nanostructure material to associate with and/or store redox active species (e.g., between interlayer spaces). In some cases, the redox active species may be lithium. In some cases, the composition may be used to store charge, e.g., by incorporating the material into a charge storage device. In some cases, the charge storage device is a capacitor and/or an electrochemical double layer capacitor.

The properties of the compositions described herein may be tuned based on the substitution of the carbonyl functional group. Those skilled in the art would recognize what types of functional groups would afford a particular, desired property, such as the ability to act as a filter or to determine an analyte or other species. In one set of embodiments, the composition may be functionalized with a binding site for determination of a target analyte. For example, a sample suspected of containing an analyte may be exposed to a composition as described herein. The analyte may interact with the composition to cause a change in a property of the composition, such as an optical property or an electrochemical property, wherein the change in the property may then determine the analyte. As used herein, the term "determination" or "determining" generally refers to the analysis of a species or signal, for example, quantitatively or qualitatively, and/or the detection of the presence or absence of the species or signals. "Determination" or "determining" may also refer to the analysis of an interaction between two or more species or signals, for example, quantitatively or qualitatively, and/or by detecting the presence or absence of the interaction.

In some embodiments, the interaction between the composition and an analyte may comprise formation of a bond, such as a covalent bond (e.g. carbon-carbon, carbon-oxygen, oxygen-silicon, sulfur-sulfur, phosphorus-nitrogen, carbon-nitrogen, metal-oxygen or other covalent bonds), an ionic bond, a hydrogen bond (e.g., between hydroxyl, amine, carboxyl, thiol and/or similar functional groups, for example), a dative bond (e.g. complexation or chelation between metal ions and monodentate or multidentate ligands), or the like. The interaction may also comprise Van der Waals interactions. In one embodiment, the interaction comprises forming a covalent bond with an analyte. The binding site may also interact with an analyte via a binding event between pairs of biological molecules. For example, the composition may comprise an entity, such as biotin that specifically binds to a complementary entity, such as avidin or streptavidin, on a target analyte.

In some cases, the composition may comprise a biological or a chemical molecule able to bind to another biological or chemical molecule in a medium (e.g., solution, vapor phase, solid phase). For example, the binding site may be a functional group, such as a thiol, aldehyde, ester, carboxylic acid, hydroxyl, or the like, wherein the functional group forms a bond with the analyte. In some cases, the binding site may be an electron-rich or electron-poor moiety within the composition, wherein interaction between the analyte and the composition comprises an electrostatic interaction. For example, the composition may include an electron-donating group and the analyte may include an electron-withdrawing group. Alternatively, the composition may include an electron-withdrawing group and the analyte may include an electron-donating group.

The composition may also be capable of biologically binding an analyte via an interaction that occurs between pairs of biological molecules including proteins, nucleic acids, glycoproteins, carbohydrates, hormones, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair.

Figure 9:
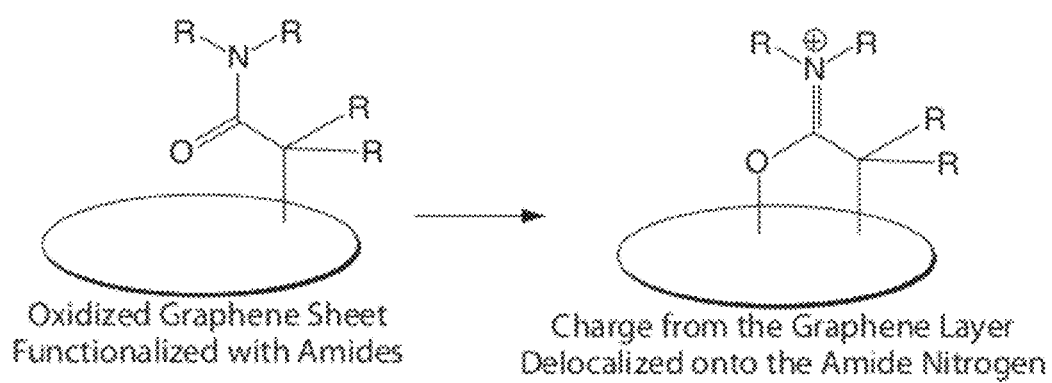
FIG. 9 shows an oxidized graphene sheet functionalized with amide groups undergoing a redox reaction such that charge from the graphene layer is delocalized onto the amide nitrogen.

In some cases, the carbonyl functional groups may be further functionalized to incorporate functional groups capable of undergoing redox reactions (e.g., conducting polymer), which may lead to enhancement of the charge storage of these compositions. For example, bound amides may produce cyclic structures wherein the oxygen binds to cationic charges in a graphene layer that delocalizes the charge onto the nitrogen atoms and can thereby enhance the charge storage capabilities of the graphene. FIG. 9 shows an illustrative embodiment, where an oxidized graphene sheet functionalized with amide groups may undergo a redox reaction such that charge from the graphene layer is delocalized onto the amide nitrogen.

Accordingly, in some embodiments, the carbonyl species may be functionalized with an electrochemically active functional group. Non-limiting examples of electrochemically active functional groups include conducting polymers, metals, semi-metals, and/or semiconductors. In some cases, the functionalization contains amides which can form cyclic structures with the carbon-based nanostructure, wherein the oxygen binds to cationic charges in the carbon nanostructure. In some cases, the electrochemically active species is a species typically used in batteries and would be readily identified by those skilled in the art.

In some embodiments, the composition may be appropriately functionalized to impart desired characteristics (e.g., surface properties) to the composition. In some embodiments, the composition may include compounds, atoms, or materials that can alter or improve properties such as compatibility with a suspension medium (e.g., water solubility, water stability), photo-stability, and biocompatibility. In some cases, the composition comprises functional groups selected to possess an affinity for a surface. For example, the composition may also be functionalized to facilitate adsorption onto a particular surface, such as the surface of a substrate. In some embodiments, the composition is functionalized with carboxylic acid moieties, which may allow for electrostatic adsorption onto charged surfaces, such as glass surfaces, particle surfaces, and the like.

Figure 8:
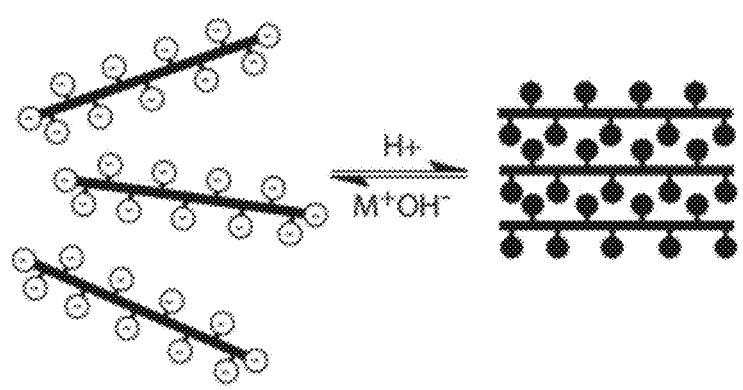
FIG. 8 shows an illustrative example of protonated and unprotonated forms of functionalized graphene, according to some embodiments.

In some cases, the carbonyl species may be functionalized such that the graphene material is at least partially or substantially water-soluble. Examples include embodiments where the functional groups are —$CH_2C(=O)NMe_2$ or —$CH_2C(=O)OR^a$, where $R^a$ is hydrogen, alkyl, alkenyl, alkynyl, or aryl, any of which is optionally substituted, In some embodiments, the functional groups may be saponified to form —$CH_2CO_2H$ groups or a salt thereof. In such embodiments, the pH of a resulting solution of the graphene may be increased or decreased, thereby causing the carboxylic acid moieties to be either protonated or unprotonated. In some cases, the ability to alter between protonated and unprotonated forms of the graphene may aid in the purification, solubility, and/or stability of the graphene. For example, the protonated form may be substantially insoluble in water and/or layers of the graphene may associated with each other, such that small colloids and/or clusters of the graphene may form. In the unprotonated form, each graphene sheet may comprise a plurality of negative charges, such that the graphene is soluble or substantially soluble in water and/or each graphene layer is not associated with any other layers or graphene materials (e.g., due to electrostatic repulsions of the layers). For example, see FIGS. 8 and 13 for illustrated examples of this process. Such a transition (e.g., from substantially soluble or soluble, to substantially insoluble or insoluble) may aid in purification of the material (e.g., by filtration, washing, etc.). Those of ordinary skill in the art will be aware of methods for saponifying amides (e.g., in the presence of a base at elevated temperatures, for example, KOH in EtOH/$H_2O$ at reflux).

Some embodiments provide stable, aqueous colloids or emulsions comprising graphene species capable of remaining in solution without the need for polymeric or surfactant stabilizers. The graphene species may be substituted, for example, on the basal plane by allylic carboxylate groups. In some embodiments, the stability of an emulsion and/or colloidal suspension may be determined based on the zeta-potential of the emulsion and/or colloidal suspension. Generally, emulsion/colloidal suspension having a zeta-potential of about ±40 mV or greater are considered to have good stability. In some cases, the zeta-potential of the emulsion or colloid may be about ±20 mV, about ±30 mV, about ±35 mV, about ±40 mV, about ±45 mV, about ±50 mV, about ±55 mV, about ±60 mV, about ±65 mV, about ±70 mV, or greater.

In some cases, the compositions may include positively and/or negatively charged functional groups.

The compositions and materials described herein may serve as effective substrates for reducing the amount of, or even removing, a substance (e.g., toxic compounds) from a sample. In some cases, the sample is a vapor phase sample. In some embodiments, the sample is a liquid sample. In some embodiments, the sample is an aerosol sample. The term "sample" refers to any material (e.g., in vapor phase, liquid phase, solid phase, aerosols, etc.) containing a species to be determined (e.g., an analyte), purified, filtered, absorbed, adsorbed, chemically altered, or otherwise advantageously evaluated in accordance with the embodiments described herein. In some cases the sample is a vapor phase sample drawn or derived from a composition or device comprising nicotine (e.g., a cigarette). In some cases, the sample may be drawn from a water supply.

For example, the method may involve contacting a vapor phase sample containing a first concentration of the species with a composition comprising substituted graphene or graphene oxide molecules. Upon contacting the concentration, the vapor phase sample may have a second, decreased concentration of the species. In some embodiments, the concentration of the species may be reduced by at least 5%, at least 10%, at least 20%, at least 30%, at least 40%, at least 50%, at least 60%, at least 70%, at least 80%, at least 90%, at least 95%, or, in some cases, at least 99%.

Without wishing to be bound any theory, the functionalized graphenes or graphene oxides described herein may be particularly effective in the removal or reduction in the amount of a substance in sample as the intersheet distance between adjacent graphene or graphene oxide molecules may be advantageously varied (e.g., increased, decreased) to suit a particular application, based on the functionalization on the basal plane of the graphene or graphene oxide sheets. For example, the graphene or graphene oxide sheets or may exhibit increased surface area to due at least in part to an increase in intersheet distance between graphene molecules or graphene oxide molecules. This may be attributed to functionalization on the basal plane of the graphene or graphene oxide sheets by sterically large functional groups, and may advantageously allow for increased interaction (e.g., van der Waals interactions) between the composition and the sample. In some embodiments, the functional groups may be selected to have a particular size to produce an intersheet distance capable of trapping or sequestering a particular analyte or species within the composition. The ability to covalently functionalize graphene or graphene oxide sheets with a wide array of groups, as described herein, may also be advantageous as the compositions may be tailored for specific targets. For example, functional groups which have known specific interactions with potential contaminants may be appended onto graphene or graphene oxide sheets, thereby turning the graphene or graphene oxide sheet into a "super-ligand" for a wide range of substances, including toxic materials. Examples of such substances and samples are described herein. As an illustrative embodiment, a chelator such as dimercaprol or its analogs may be attached to a graphene or graphene oxide sheet in order to trap heavy metals (e.g., Cd.

In some embodiments, the compositions may be used to selectively absorb, trap, and/or filter chemicals (e.g., gases and/or liquids). For example, the carbon-based nanostructure may be functionalized with groups such as perfluoroalkyl groups and/or nitroaromatic groups, which may interact with (e.g., bind) toxins, pollutants, or other undesirable materials. The interaction may include an electrostatic interaction (e.g., between relatively electron-rich moieties of a chemical and relatively electron-poor moieties of a carbon-based nanostructure), a non-covalent interaction (e.g., binding interaction), a covalent interaction, or the like. In an illustrative embodiment, the carbon-based nanostructure may include a plurality of electron-poor nitroaromatic groups capable of interacting with (e.g., binding) electron rich groups of an organic pollutant via the nitroaromatic groups. In some embodiments, the composition may include orbitals (e.g., p-orbitals) that may sufficiently overlap with orbitals present on a particular analyte. For example, the interaction may involve pi-pi stacking between conjugated pi-system of a high surface area graphene or graphene oxide with polycyclic aromatic hydrocarbons, including undesirable components of cigarette smoke, such as benzopyrene. In some cases, the analyte may be a metal ion (e.g., a heavy metal ion) having d-orbitals which overlap with the pi-system of the functionalized graphene or graphene oxide sheets and/or various carbonyl groups on the graphene or graphene oxide sheets. Thus, compositions described herein may be useful for removing undesired chemicals from fluids or liquids.

In some embodiments, a composition described herein is used in a device which functions as a filter, catalyst, and/or sensor.

In some embodiments, a device for filtering or reducing the amount of a substance (e.g., a toxin, pollutant) in a sample may comprise a composition described herein. The device and/or composition may be contacted with a sample containing an undesired substance, such as a toxin. The substance may be introduced to a device comprising the composition, and the composition may interact with the substance such it reduces the amount of the substance that exits the device. In some cases, prior to contact with the device and/or composition, the sample may have a first concentration of a substance, and, after contacting the device and/or composition, the sample may have a second concentration of the substance, which is less than the first concentration. For example, the composition may physically prevent the substance from diffusing away from the composition by binding or otherwise interacting with the substance. In some embodiments, the composition may interact with the substance to chemically alter the substance or convert the substance into a more desirable species, as described more fully below.

In some cases, the device filters, chemically alters, and/or senses analytes and other species including pollutants, toxins, and other undesirable substances. In some cases, the analyte includes functional groups containing perfluoroalkyls or nitroaromatics. In some embodiments, the device may filter and/or sense nitroaromatic molecules and other electron-poor molecules with electron-rich functional groups.

The analyte or species may be a chemical or biological analyte. The analyte or species may be any chemical, biochemical, or biological entity (e.g. a molecule) to be analyzed, including organic species, metal-containing species, metals and metal ions, or other inorganic species. In some cases, the composition may be selected to have high specificity for the analyte. In some embodiments, the analyte comprises a functional group that is capable of interacting with at least a portion of the composition, such as a functional group positioned on a basal plane of a graphene or graphene oxide sheet. For example, the functional group may interact with the analyte by forming a bond, such as a covalent bond or a non-covalent bond. In some embodiments, the functional group may interact with the analyte by chemically altering the analyte. Some embodiments involve analytes comprising electron-withdrawing groups such as perfluoroalkyl groups and/or nitroaromatic groups.

Examples of analytes and species include, but are not limited to, various toxins, pollutants, such as tobacco-specific N-nitrosamines (TSNAs), hydrocarbons such as benzene or benzopyrene, pesticides, formaldehyde, metals including toxic metals, heavy metals, and/or radioactive metals such as arsenic, cadmium, lead 210, and the like, gases such as ammonia, carbon monoxide, hydrogen cyanide, and others. In some embodiments, the analyte is carbon monoxide. In some embodiments, the analyte is a heavy metal.

Figure 20:
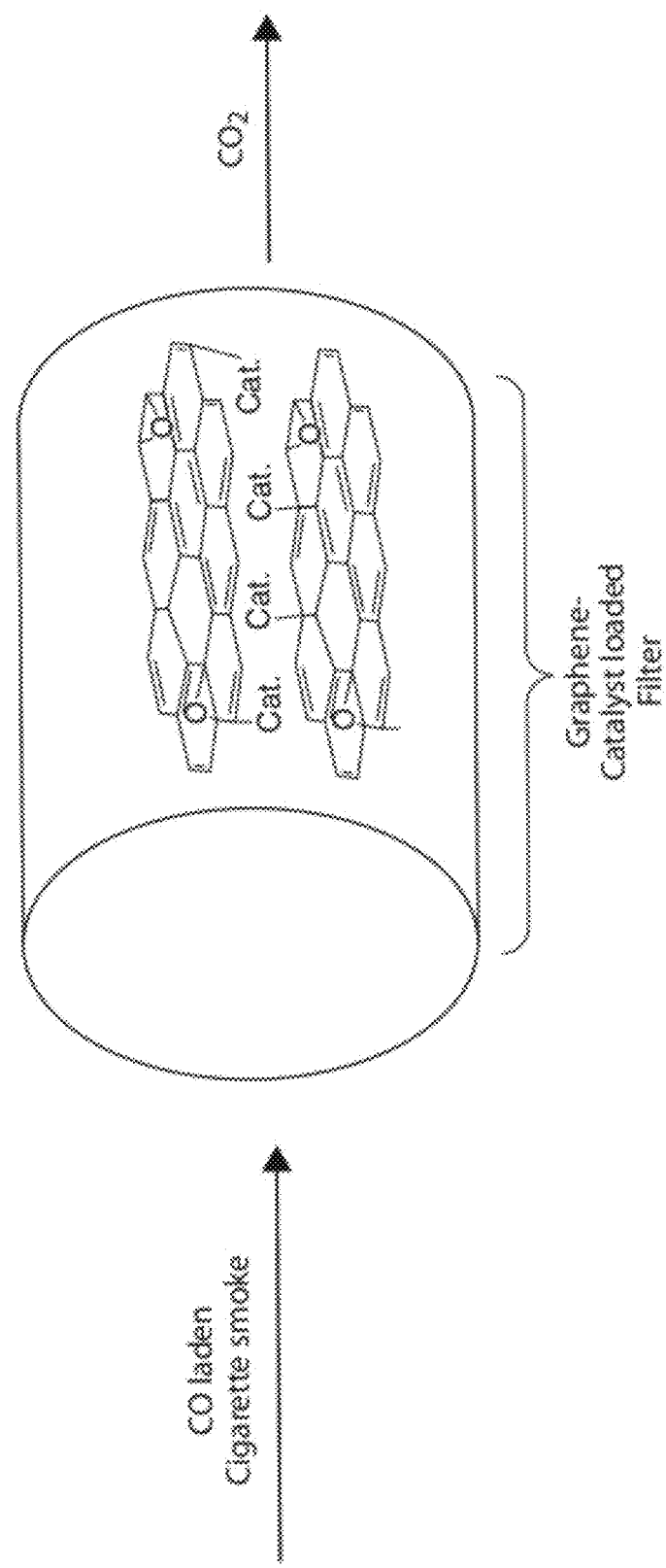
FIG. 20 shows the use of a composition described herein as a filter for cigarette smoke.

In one set of embodiments, the compositions described herein may be useful as cigarette filter materials. (FIG. 20) For example, the composition may be arranged in a cigarette, or related product or device containing nicotine, and the sample contacting the composition may be vapor generated by the cigarette, i.e., cigarette smoke. The composition may be effective in reducing the amount of undesirable substances found in cigarette smoke, including analytes as described herein.

Compositions described herein may also be appropriately functionalized to serve as catalysts or as a support material for catalysts. In some cases, the functional groups comprise catalytic metals or metal-containing groups, such as metal oxides. In certain cases, the functional groups comprise positively and/or negatively charged functional groups which may bind metal ions capable of operating as catalysts. In some cases, the functional groups function as metal binding ligands, or ligands for metal-containing groups, and comprise nitrogen, sulfur, and/or phosphorus, thereby allowing the materials to function as a catalyst. In some embodiments, the bound metal or metal-containing group (e.g., metal oxide) may be used for the reduction of oxygen (e.g., in a fuel cell). In certain cases, the bound metal may oxidize and/or reduce water to make oxygen and/or hydrogen gases. In some embodiments, the functional group may comprise a species capable of reducing or oxidizing various species, including oxygen. Without wishing to be bound by any theory, covalent functionalization of graphene or graphene oxide sheets on the basal plane may be advantageous in that the available surface area of the graphene would be altered (e.g., increased, decreased), allowing for enhanced interaction with an analyte or other sample. Additionally, the composition includes covalent, and relatively robust, attachment between the catalyst and the graphene or graphene oxide sheets, potentially resulting in a more stable system and/or enhanced catalytic rates.

As an illustrative embodiment, the compositions described herein may be used for oxidation of carbon monoxide to carbon dioxide. For example, a functionalized graphene or graphene oxide containing a catalyst (e.g., metal catalyst) may be prepared using methods described herein. Carbon monoxide may interact with the catalyst attached to the graphene or graphene oxide sheet and undergo the catalytic cycle to $CO_2$. In some cases, the composition (e.g., a composition comprising a Pd catalyst) may also be capable of reducing nitric oxide concurrently with oxidizing CO. Such methods may be useful, for example, in treating or filtering cigarette smoke to remove CO and/or NO. Those of ordinary skill in the art would be able to select various catalytic moieties capable of oxidizing CO for use in the context of the embodiments described herein. In some cases, the catalytic moiety comprises Pd, Fe, Ce, Al, Cu, or Ti, or an oxide thereof. Examples of catalysts for CO oxidation include, but are not limited to, Pd nanoclusters, $Fe_2O_3$, FeOOH, or TiOOH.

In some cases, the functional group is capable of binding a metal atom or ion, and comprises nitrogen, sulfur, and/or phosphorus. In certain embodiments, the compositions described herein are used in a fuel cell. In some instances, compositions described herein are used for the reduction of water.

In some embodiments, the composition may be employed in composites for mechanical property enhancement. For example, this may be accomplished either through a covalent linking of the carbon-based nanostructure (e.g., graphene) to the matrix or through functionalization of the carbon-based nanostructure that allows for the carbon-based nanostructures to be dispersed throughout the matrix material. Additionally the functionalization of the carbon-based nanostructure may be used to produce composites which are formed substantially from graphene or graphene oxide, wherein the graphene or graphene oxide sheets are associated with each other (e.g., via the functional groups).

Accordingly, in some embodiments, compositions described herein may be arranged in a composite material comprising a matrix material. In some cases, the carbon-based nanostructures are associated with the matrix material via at least one covalent bond. In certain embodiments, the covalent bond is form via an epoxide, amine, and/or urethane chemistries known to those skilled in the art. In some cases, a carbon-based nanostructure is functionalized such that the material can be dispersed through the matrix material. In some embodiments, the functional groups of the carbon-based nanostructure are compatible and/or the same as the functional group of the matrix material. In certain instances, the functionalization has a negative Flory interaction parameter with the matrix material. In some embodiments, a carbon-based nanostructure is linked to a second carbon-based nanostructure via the functional groups of each of the carbon-based nanostructures.

Those of ordinary skill in the art will be aware of various additional applications in which the compositions described herein may be employed and various methods and techniques for processing and forming devices comprising the compositions provided herein.

The compositions described herein may also be useful as biological imaging agents, medical diagnostic agents, or biosensors. For example, carbon-based nanostructures comprising charged moieties may be useful as DNA diagnostics, wherein selection of the charged moieties may modulate interaction of the carbon-based nanostructures with DNA molecules. The carbon-based nanostructures may be functionalized to increase or decrease electrostatic interactions of the composition with DNA. In some cases, the carbon-based nanostructures may be assembled in combination with enzymes, or other biomolecules, for sensing applications.

In another set of embodiments, the composition may be useful in coatings (e.g., electrostatic assembly). For example, a composition may be associated with a complementarily charged material (e.g., polymer, DNA, RNA, proteins, inorganic particles/clusters, individual metal ions bearing multiple charges, carbon nanotubes, fullerenes, graphene, etc.). For example, the complementarily charged material may be positively charged and the composition may comprise negatively charged moieties, such the composition associated with the material and forms a coating on the material. In some cases, the coating may substantially encapsulate the material.

In some cases, the compositions may be used in optical applications. In some embodiments, the compositions may have anisotropic structures that may interact with light (e.g., polarized light) selectively and give rise to polarized dependent properties.

In another set of embodiments, functionalized carbon-based nanostructure may be useful as electron transport materials in photovoltaic devices. The functionalized carbon-based nanostructure may be combined with a material such as a conducting polymer, wherein the carbon-based nanostructure are functionalized with functional groups facilitating the stable formation of polymer blends, as described herein. In operation, the polymer matrix may act as an electron donor while the carbon-based nanostructure may act as the electron acceptors, wherein the carbon-based nanostructures enhance the electron mobility through the device, resulting in photovoltaic devices having improved performance.

Compositions described herein may be useful in other applications, including chemical sensors, transistors (e.g., organic transistors), transparent conductive coatings, electrodes (e.g., for electrocatalysis), components in photovoltaic devices, light-emitting diodes (e.g., OLEDs, PLEDs, etc.), semiconductors, reinforcing elements for polymers including high strength polymers, composites, displays, actuators (e.g., polymer mechanical actuators), energy storage/production, circuits, flame retardant materials, and emissive elements. In some cases, the compositions may be useful in cosmetic compositions. In certain embodiments, the compositions may exhibit ion exchange properties and may be useful in water purification. Many other applications could benefit from the methods and compositions described herein, including electronic materials for the semiconductor industry, gas-transport barrier agents for thermoplastic and thermoset resins (e.g., for food and beverage packaging), flame retardants, additives for automotive fuel lines and gas tanks (e.g., as electrostatic discharge protection), additives for increased modulus and electrical conductivity (e.g., for electrostatic painting) in automotive body panels, conductive adhesives, and electrode materials for rechargeable batteries and capacitors According to certain embodiments of the invention, a graphene dispersion or other dispersion using carbon-based nanostructures such as those discussed herein may be used in the application of thin coatings which could produce flexible, conductive, transparent electrodes (i.e. replacements for indium tin oxide coatings), conductive barrier in OLED and organic photovoltaic (OPV) devices, non-halogenated fire retardant coatings, as well as electrostatic discharge protection for plastics, e.g., due to the ability to control the spacing of such nanostructures within a material. Products such as moisture and oxygen barrier sealants for the organic photovoltaic (PV) and light emitting diode markets can also be produced in some cases. Charge storage devices such as ultracapacitors and rechargeable batteries can be produced that use graphene or other compositions as described herein, e.g., as electrodes, in accordance with certain embodiments of the invention. The ability to chemically exfoliate and modify the surface of certain graphene structures and reassemble the modified structures into a layered structure with specific inter-planar spacing may be used within such energy-storage devices, e.g., by allowing ions to be contained within such layered structures. In certain embodiments, the ability to controllably functionalize the surface of certain graphene structures, and/or their spacing, allows the structures to be dispersed into a plastic or a polymer to modifying its strength, fracture toughness, heat distortion temperature, moisture or oxygen diffusivities, and/or conductivities (both thermal and electrical). For example, a particular spacing of graphene structures may be selected in order to cause a polymer containing the graphene structure to exhibit a certain ionic or electrical conductivity therein.

The methods of forming functionalized carbon-based nanostructures and/or various embodiments described herein may be carried out in any suitable solvent, or combination thereof. Examples of solvents that may be suitable for use in the invention include, but are not limited to, benzene, p-cresol, toluene, xylene, mesitylene, diethyl ether, glycol, petroleum ether, hexane, cyclohexane, pentane, dichloromethane (or methylene chloride), chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, mixtures thereof, or the like.

The methods described herein may be carried out at any suitable temperature(s). In some cases, the reaction is carried out at about room temperature (e.g., about 25° C., about 20° C., between about 20° C. and about 25° C., or the like). In some cases, however, the reaction may be carried out at a temperature below or above room temperature, for example, at about −70° C., about −50° C., about −30° C., about −10° C., about −0° C., about 10° C., about 30° C., about 40° C., about 50° C., about 60° C., about 70° C., about 80° C., about 90° C., about 100° C., about 120° C., about 140° C., or the like. In some embodiments, the reaction may be carried out at more than one temperature (e.g., reactants added at a first temperature and the reaction mixture agitated at a second wherein the transition from a first temperature to a second temperature may be gradual or rapid).

A reaction may be allowed to proceed for any suitable period of time. In some cases, the reaction is allowed to proceed for about 10 minutes, about 20 minutes, about 30 minutes, about 40 minutes, about 50 minutes, about 1 hour, about 2 hours, about 4 hours, about 8 hours, about 12 hours, about 16 hours, about 24 hours, about 28 hours, or the like. In some cases, aliquots of the reaction mixture may be removed and analyzed at an intermediate time to determine the progress of the reaction.

As used herein, a "carbon-based nanostructure" refers to a carbon-containing structure comprising a fused network of rings, such as aromatic rings. In some embodiments, the carbon-based nanostructure comprises a fused network of at least 10, at least 20, at least 30, at least 40, or, in some cases, at least 50 rings, at least 60 rings, at least 70 rings, at least 80 rings, at least 100 rings, or more. The carbon-based nanostructure may be substantially planar or substantially non-planar, or may comprise planar and/or non-planar portions. The carbon-based nanostructure may optionally comprise a border at which the fused network terminates. For example, a sheet of graphite is a planar carbon-based nanostructure comprising a border at which the fused network terminates, while a fullerene is a nonplanar carbon-based nanostructure which lacks such a border. In some cases, the border may be substituted with hydrogen atoms. In some cases, the border may be substituted with groups comprising oxygen atoms (e.g., hydroxyl). In other cases, the border may be substituted as described herein. The term "fused network" does not include, for example, a biphenyl group, wherein two phenyl rings are joined by a single bond and are accordingly not fused together. Two rings are "fused" when there is at least one atom present within the structure that can be simultaneously thought of as integrally defining each of the two rings. In some cases, the fused network may substantially comprise carbon atoms. In other cases, the fused network may comprise carbon atoms and heteroatoms. Some examples of carbon-based nanostructures include graphene, carbon nanotubes (e.g., single-walled carbon nanotubes (SWCNTs), multi-walled carbon nanotubes (MWCNTs)), fullerenes, and the like, as describe more herein. Also, as noted above, other carbon-based materials (e.g. which may not necessarily comprise nanostructures), such as carbon fibers, carbon fiber paper, activated carbon, and other materials that comprise carbon-based structures comprising a fused network of rings (e.g., aromatic rings) may be used in conjunction with the methods and compositions of the present invention.

In some cases, the carbon-based nanostructure has an average maximum cross-sectional dimension of no more than about 1000 nm. In some cases, however, the maximum cross-sectional dimension may be greater than about 1000 nm, for example, the carbon-based nanostructure has an average maximum cross-sectional dimension of no more than about 1 µm, about 2 µm, about 3 µm, about 4 µm, about 5 µm, about 10 µm, or greater. In some embodiments, the carbon-based nanostructure may comprise at least about 30%, at least about 40%, at least about 50%, at least about 60%, at least about 70%, at least about 80%, at least about 90%, or at least about 95% of carbon by mass, or more. As used herein, the "maximum cross-sectional dimension" refers to the largest distance between two opposed boundaries of an individual structure that may be measured.

In some cases, the carbon-based nanostructure may comprise a nonplanar portion, e.g., a curved portion having a convex surface and a concave surface (where "surface," in this context, defines a side of a molecule or sheet defining a carbon-based nanostructure). Examples of carbon-based nanostructures comprising non-planar portions include fullerenes, carbon nanotubes, and fragments thereof, such as corannulene. In some cases, the nonplanar aromatic portion may comprise carbon atoms having a hybridization of $sp^{2-x}$, wherein x is between 1 and 9, i.e., the carbon atom may have hybridization between $sp^2$- and $sp^3$-hybridization, where this hybridization is characteristic of non-planarity of the molecule as would be understood by those of ordinary skill in the art. In these embodiments, x can also be between 2 and 8, between 3 and 7, or between 4 and 6. x may also be 1, 2, 3, 4, 5, 6, 7, 8, or 9, or fractions thereof. Typically, planar aromatic groups and polycyclic aromatic groups (e.g., phenyl, naphthyl) may comprise carbon atoms having $sp^2$ hybridization, while non-aromatic, non-planar groups (e.g., alkyl groups) may comprise carbon atoms having $sp^3$ hybridization. For carbon atoms in a nonplanar aromatic group, such as a nonplanar portion of a carbon-based nanostructure, $sp^2$-hybridized carbon atoms may be distorted (e.g., bent) to form the nonplanar or curved portion of a carbon-based nanostructure. Without wishing to be bound by theory, this distortion may cause angle strain and may alter the hybridization of the carbon atoms. As a result, the reactivity of the strained carbon atoms may be enhanced.

In some cases, the carbon-based nanostructure may comprise an elongated chemical structure having a diameter on the order of nanometers and a length on the order of microns (e.g., tens or microns, hundreds of microns, etc.), resulting in an aspect ratio greater than 10, 100, 1000, 10,000, or greater. In some cases, the carbon-based nanostructure may have a diameter less than 1 µm, less than 100 nm, 50 nm, less than 25 nm, less than 10 nm, or, in some cases, less than 1 nm. For example, the carbon-based nanostructure may have a cylindrical or pseudo-cylindrical shape (e.g., carbon nanotube).

In some cases, the carbon-based nanostructure comprises graphene (e.g., graphene nanosheets). As used herein, the term "graphene" is given its ordinary meaning in the art and refers to polycyclic aromatic molecules in which a plurality of carbon atoms is covalently bound to each other. The covalently bound carbon atoms form repeating units that comprise 6-membered rings, but can also form 5-membered rings and/or 7-membered rings. Accordingly, in graphene it appears as if the covalently bound carbon atoms (usually, $sp^2$ carbons atoms) form a single layer having a basal plane comprising a fused network of aromatic rings. Graphene typically includes at least one basal plane containing interior carbon atoms of the fused network, and a perimeter or edge containing the terminal carbon atoms of the fused network. Generally, the side ends or edges of the graphene are saturated with hydrogen atom. However, the graphene material may contain non-carbon atoms at its edges, such as OH and COOH functionalities. It should be noted that the term "graphene" includes reference to both single atom layers of graphene and multiple layer stacks of graphene.

In some cases, the carbon-based nanostructure is a carbon nanotube. As used herein, the term "carbon nanotube" is given its ordinary meaning in the art and refers to a substantially cylindrical molecule comprising a fused network of six-membered aromatic rings. In some cases, carbon nanotubes may resemble a sheet of graphite rolled up into a seamless cylindrical structure. It should be understood that the carbon nanotube may also comprise rings other than six-membered rings. Typically, at least one end of the carbon nanotube may be capped, i.e., with a curved or nonplanar aromatic group, although in other embodiments, the carbon nanotube need not be capped. Carbon nanotubes may have a diameter of the order of nanometers and a length on the order of micrometers, resulting in an aspect ratio greater than 100, 1000, 10,000, or greater. The term "carbon nanotube" includes single-walled nanotubes (SWCNTs), multi-walled nanotubes (MWCNTs) (e.g., concentric carbon nanotubes), inorganic derivatives thereof, and the like. In some embodiments, the carbon nanotube is a single-walled carbon nanotube. In some cases, the carbon nanotube is a multi-walled carbon nanotube (e.g., a double-walled carbon nanotube).

In some cases, the carbon-based nanostructure is a fullerene. As used herein, the term "fullerene" is given its ordinary meaning in the art and refers to a substantially spherical molecule generally comprising a fused network of five-membered and/or six-membered aromatic rings. For example, $C_{60}$ is a fullerene which mimics the shape of a soccer ball. The term fullerene may also include molecules having a shape that is related to a spherical shape, such as an ellipsoid. It should be understood that fullerenes may comprise rings other than five- or six-membered rings. In some embodiments, the fullerene may comprise seven-membered rings, or larger. Fullerenes may include $C_{36}$, $C_{50}$, $C_{60}$, $C_{70}$, $C_{76}$, $C_{84}$, and the like.

As noted above, carbon-based nanostructures described herein may have a high density of charged moieties, i.e., may have a high ratio of charged moieties to double bonds on the outer surface of the carbon-based nanostructure. Those of ordinary skill in the art will be able to determine the ratio of charged moieties to double bonds on the outer surface of the carbon-based nanostructure. For example, the number and type of atoms or groups present within a carbon-based nanostructure can be determined using differential scanning calorimetery thermogravimetric analysis, spectrophotometric measurements, elemental analysis, etc. In one example, a carbon-based nanostructure may be analyzed via elemental analysis in order to calculate the ratio of charged moieties to double bonds on the outer surface of the carbon-based nanostructure may be calculated.

In some cases, the carbon-based structure is a carbon fiber. As used herein, the term "carbon fiber" is given its ordinary meaning in the art and refers to filamentary materials comprising carbon. In some cases, the carbon fiber includes at least about 50, 60, 70, 80, 90, or 95% by weight carbon. In some cases, the carbon fiber is in the form of filamentary tows having a plurality of individual filaments. The diameter of the carbon fibers may be between about 1 um and about 1 mm, between about 5 um and about 100 µm, between about 5 µm and about 10 µm. In some cases, a plurality of carbon fibers may form carbon fiber paper, i.e., a two-dimensional sheet of carbon fibers. The fibers may be arranged randomly within the plane of the sheet.

As used herein, the term "react" or "reacting" refers to the formation of a bond between two or more components to produce a stable, isolable compound. For example, a first component and a second component may react to form one reaction product comprising the first component and the second component joined by a covalent bond. The term "reacting" may also include the use of solvents, catalysts, bases, ligands, or other materials which may serve to promote the occurrence of the reaction between component(s). A "stable, isolable compound" refers to isolated reaction products and does not refer to unstable intermediates or transition states. A variety of functional groups may be installed on the carbon-based nanostructure by varying the alkyne (e.g., electrophile) and nucleophile.

As used herein, the term "reacting" refers to the formation of a bond between two or more components to produce a compound. In some cases, the compound is isolated. In some cases, the compound is not isolated and is formed in situ. For example, a first component and a second component may react to form one reaction product comprising the first component and the second component joined by a covalent bond. That is, the term "reacting" does not refer to the interaction of solvents, catalysts, bases, ligands, or other materials which may serve to promote the occurrence of the reaction with the component(s).

The term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and can not be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

The term "aliphatic," as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl," "alkynyl" and the like. Furthermore, as used herein, the terms "alkyl," "alkenyl," "alkynyl" and the like encompass both substituted and unsubstituted groups. In certain embodiments, as used herein, "lower alkyl" is used to indicate those alkyl groups (substituted or unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic," as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl, cyclohexyl, —$CH_2$-cyclohexyl, cyclohexenylethyl, cyclohexanylethyl, norborbyl moieties and the like, which again, may bear one or more substituents.

The term "heteroalkyl" is given its ordinary meaning in the art and refers to alkyl groups as described herein in which one or more atoms is a heteroatom (e.g., oxygen, nitrogen, sulfur, and the like). Examples of heteroalkyl groups include, but are not limited to, alkoxy, poly(ethylene glycol), alkyl-substituted amino, tetrahydrofuranyl, piperidinyl, morpholinyl, etc.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CHF_2$; —$CH_2F$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the term "aryl," as used herein, refers to a stable mono- or polycyclic, unsaturated moiety having preferably 3-14 carbon atoms, each of which may be substituted or unsubstituted. In certain embodiments, the term "aryl" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic," and is encompassed by the term "alicyclic."

In general, the term "heteroaryl", as used herein, refers to a stable mono- or polycyclic, unsaturated moiety having preferably 3-14 carbon atoms, each of which may be substituted or unsubstituted; and comprising at least one heteroatom selected from O, S, and N within the ring (i.e., in place of a ring carbon atom). In certain embodiments, the term "heteroaryl" refers to a planar ring comprising at least one heteroatom, having p-orbitals perpendicular to the plane of the ring at each ring atom, and satisfying the Huckel rule where the number of pi electrons in the ring is (4n+2) wherein n is an integer.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl) aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "cycloalkyl," as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$ (CO)R$_x$, wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic," as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7-membered ring or a polycyclic group wherein at least one ring atom is a heteroatom selected from O, S, and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with, but are not limited to, aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples or generally applicable substituents are illustrated by the specific embodiments described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments described herein.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino," as used herein, refers to a primary (—NH$_2$), secondary (—NHR$_x$), tertiary (—NR$_x$R$_y$), or quaternary (—N$^+$R$_x$R$_y$R$_z$) amine, where R$_x$, R$_y$, and R$_z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "alkyne" is given its ordinary meaning in the art and refers to branched or unbranched unsaturated hydrocarbon groups containing at least one triple bond. Non-limiting examples of alkynes include acetylene, propyne, 1-butyne, 2-butyne, and the like. The alkyne group may be substituted and/or have one or more hydrogen atoms replaced with a functional group, such as a hydroxyl, halogen, alkoxy, and/or aryl group.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In other embodiments, the alkyl, alkenyl, and alkynyl groups employed in the invention contain 1-8 aliphatic carbon atoms. In still other embodiments, the alkyl group contains 1-6 aliphatic carbon atoms. In other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkoxy" refers to the group, —O-alkyl. The term "aryloxy" refers to the group, —O-aryl. The term "acyloxy" refers to the group, —O-acyl.

The term "independently selected" is used herein to indicate that the R groups can be identical or different.

These and other aspects described herein will be further appreciated upon consideration of the following Examples, which are intended to illustrate certain particular embodiments of the invention but are not intended to limit its scope, as defined by the claims.

Example 1

Figure 10:
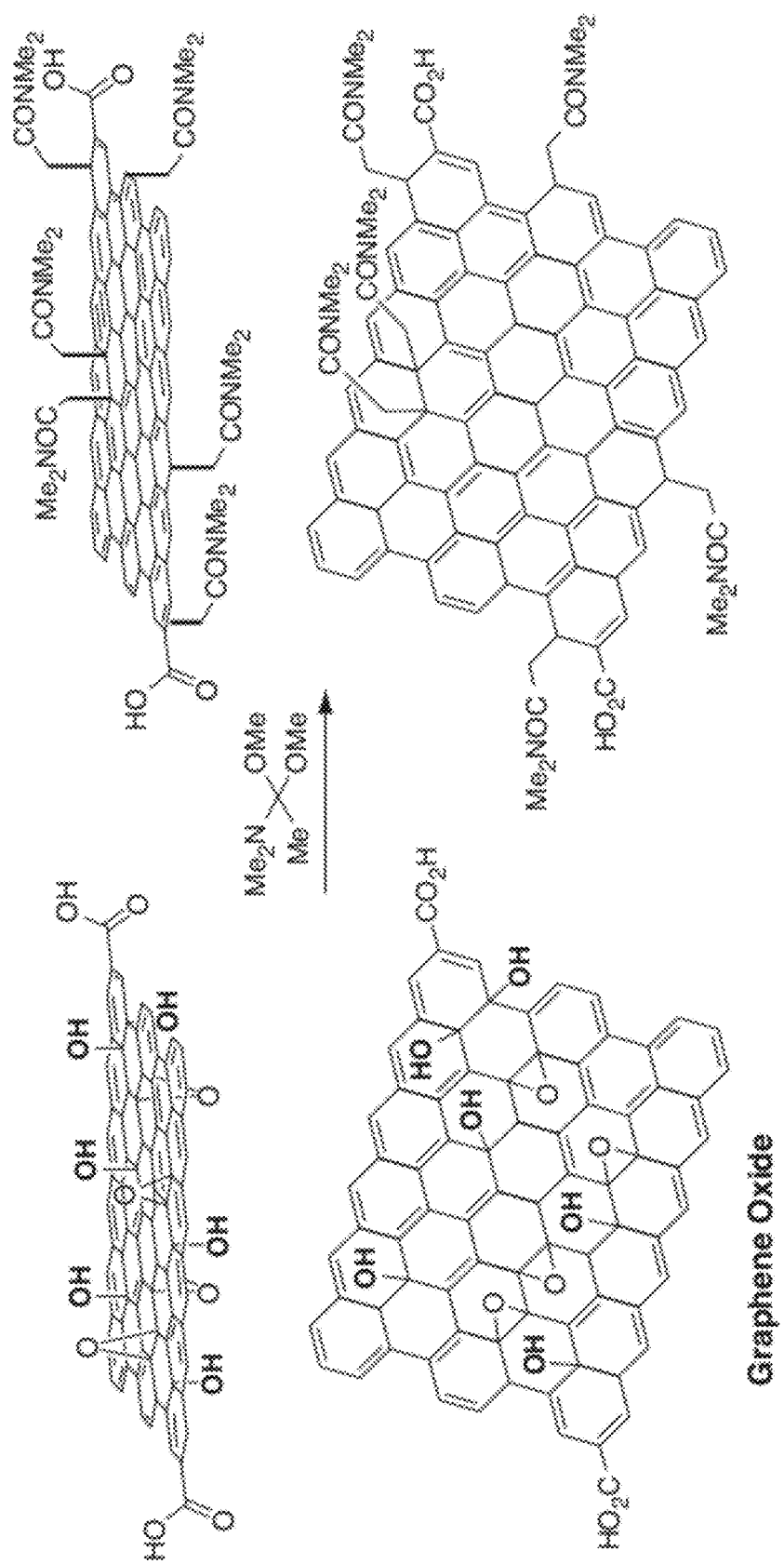
FIG. 10 shows the conversion of carbon-oxygen bonds on a graphite oxide basal plane to carbon-bound carbonyl groups.

The following example describes the direct conversion of carbon-oxygen bonds on a graphite oxide basal plane to carbon bound carbonyl groups (e.g., see FIG. 10). GO (graphene oxide) in this example was functionalized using a Claisen rearrangement to allylically transpose tertiary alcohol functional groups found throughout the basal plane of graphite oxide into carbon-bound carbonyl derivatives. In traditional Claisen rearrangements, a vinyl allyl alcohol is heated to simultaneously break a carbon-oxygen bond while forming a carbon-carbon bond (via a sigmatropic rearrangement). In this example the tertiary alcohols that adorn the surface of graphite oxide function as the tertiary allylic alcohols. Direct treatment of these functional groups with a vinyl group equivalent (e.g., dimethylacetamide dimethylacetal is shown in FIG. 10) forms a vinyl allyl alcohol on GO, in situ. Heating this modified GO then directly breaks the tertiary alcohol bond and allylically forms a new carbon-carbon bond while simultaneously forming the new carbonyl derivative. In the FIG. 10, the newly formed carbonyl derivative is an N,N-dimethylamide.

Functional density determination (the extent of functionalization, or "yield") was carried out through the use of X-ray photoelectronic spectroscopy (XPS), thermogravemetric analysis (TGA), X-ray diffraction (XRD), Raman spectroscopy, and Fourier transform infrared spectroscopy (FTIR). Analysis of the rearranged material indicated that not only were carbonyl derivatives being successfully incorporated into the graphene surface, but that the remaining, unreacted oxygen functionality was being reduced during the course of the reaction. Therefore, this method simultaneously acts as a functionalization process as well as a reduction process. Comparatively, this method reduces the graphene oxide to an equivalent degree to the most common chemical reduction method utilizing hydrazine.

A variety of other reagents may be used to transform the allylic tertiary alcohols on the surface of GO to vinyl allyl alcohols for subsequent Claisen rearrangement. In particular, triethylorthoformate, trimethylorthoformate, $CH_3C(OCH_3)_3$ and ethylacetoacetate in combination with a weak Bronsted acid source may produce ester groups on the surface of graphene. Additionally, phenyl vinyl sulfoxides and ammonium betaines (e.g. 3-(trimethylammonio)acrylate) may produce aldehyde functionality on the surface of graphene. Vinyl alcohol groups in the presence of palladium and mercury catalysts can also be used to form the necessary vinyl allyl alcohol on GO.

Exemplary Methodology:

350 mg of graphite oxide and 350 mL of an appropriate dried and degassed solvent (tetrahydrofuran-THF, dioxane, bis(2-methoxyethyl)ether) were added to a flame dried and argon filled flask. The solution was sonicated for 1 hour in a bath sonicator to achieve a fine dispersion. The solution was then brought to reflux and the dimethylacetamide dimethylacetal 2.4 mL (15.7 mmol, 2 times molar mass of oxygen content in GO starting material). The mixture was refluxed for 24 h then cooled to room temperature. The dispersion was filtered through an anodesic membrane (0.2 micron pore diameter) to obtain a filter cake. The material was then washed with copious amounts of acetone followed by sonication in 20 mL of acetone for 1 h. The slurry was centrifuged at 14,500 rpm to obtain a black sediment. Sonication in acetone and centrifugation was repeated 3 times with acetone, 2 times with water and again 2 times with acetone. The final sediment was dried under vacuum in 40 degrees over KOH pellets.

Incorporation of carbonyl functionalized graphene derivatives as an electronic component into devices allows graphene derivatives to be used in a variety of applications. One such application would be in replacing graphite as the commercial anode material for lithium ion batteries. In this context many attributes of the functionalized graphene derivatives described above (carbonyl binding groups, large intersheet spacing, nanosheet structure, conductivity) should allow for high levels of lithium storage/intercalation into the nanosheets. Another application is the formation/binding of metallic nanoparticles on the surface of the modified graphene sheets. Not only could a nanoparticle-graphene derivative composite be produced by mixing the two substrates, but the carbonyl functionality can also serve to "seed" the formation of nanoparticles. In a similar capacity, the graphene derivatives can be used to chemically sense individual metal ions by measuring changes in the conductivity of the graphene sheet upon binding the various metals. When bound to metal ions the graphene derivative can serve as a scaffold for catalytic processes. This is relevant for redox-type reactions in which, after the reaction, reduction of the metal ion can occur electrochemically through the graphene backbone. Finally, the graphene derivatives can be utilized to serve as electron transport semiconductors (n-type materials) in quantum dot based photovoltaic devices.

Example 2

The following example described characterization of functionalized nanostructures formed using and/or comprising certain compositions of the present invention.

Reaction conditions for this example are substantially similar as described in Example 1, except for variations in the solvent and temperature. In addition, control reactions were carried out (e.g., wherein no DMADMA was added to the reaction mixture).

Figure 2A:
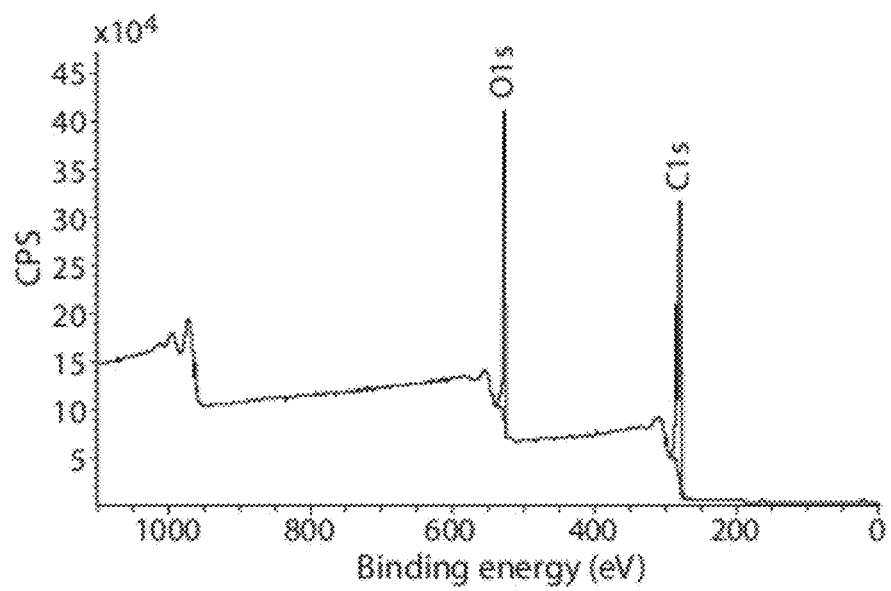
FIGS. 2A-2B show XPS data of materials, including materials of the present invention, according to some embodiments.
Figure 2B:
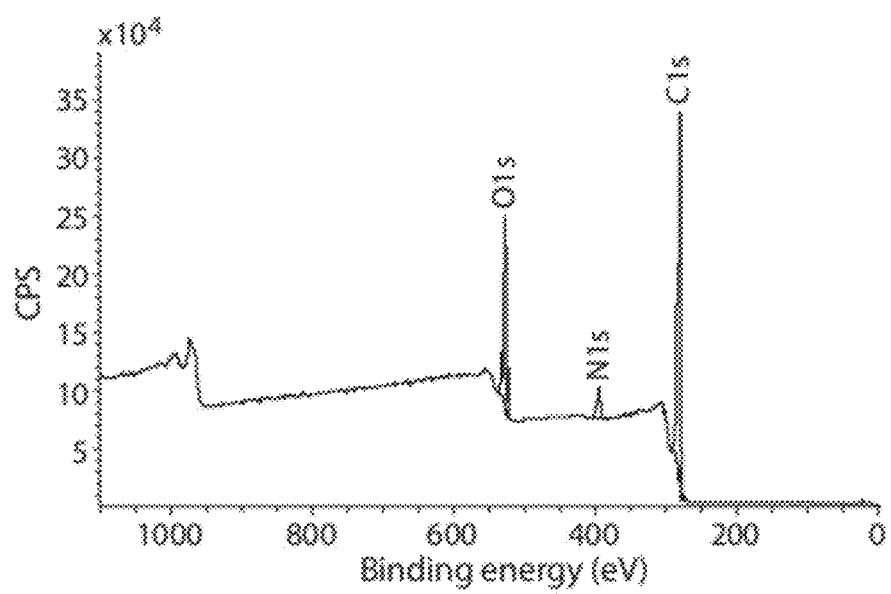

In this example, the following abbreviations are employed, and are further described herein:
rGO1—reaction in THF at 60° C., DMADMA added
rGO1c—control reaction in THF at 60° C., no DMADMA added
rGO2—reaction in 1,4-dioxane at 100° C., DMADMA added
rGO2c—control reaction in 1,4-dioxane at 100° C., no DMADMA added
rGO3—reaction in diglyme at 150° C., DMADMA added
rGO3c—control reaction in diglyme at 150° C., no DMADMA added)
rGO3b—reaction in diglyme sonicated for 3 h at pH=9
rGO3b (500)—sample annealed in 500° C. for 6 h in $N_2$ atmosphere Characterization:

Throughout the course of the reaction, the reaction mixture turns black shortly after addition of DMA (FIG. 2). The rate of color change is highest for highest reaction temperature indicating possible deoxygenation of GO. Specifically, FIG. 2 shows the reaction mixture (rGO3) before (on the left) and 60s after (on the right) addition of DMA.

Figure 3A:
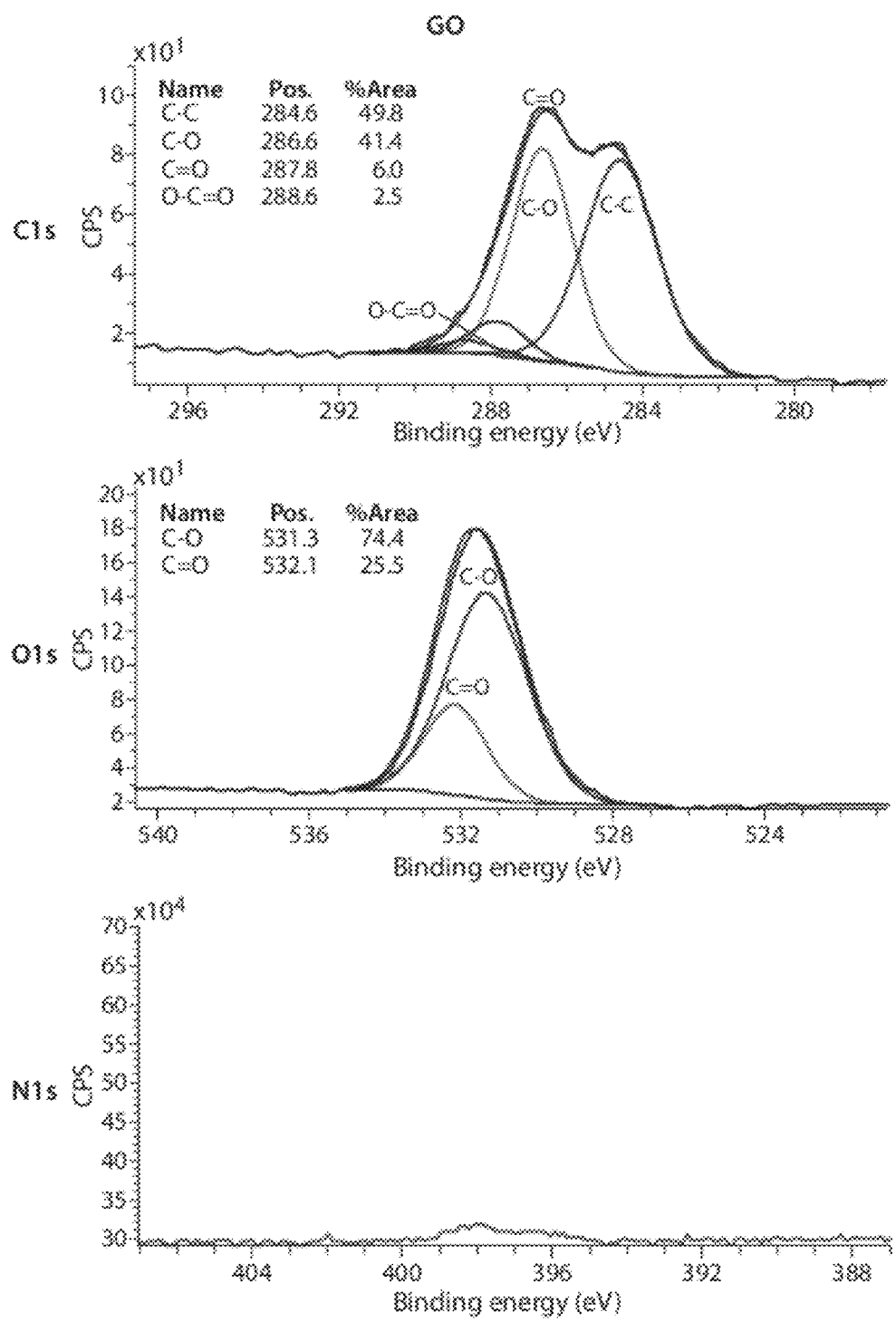
FIGS. 3A-3B show hi-res XPS data of materials, including materials of the present invention, according to some embodiments.
Figure 3B:
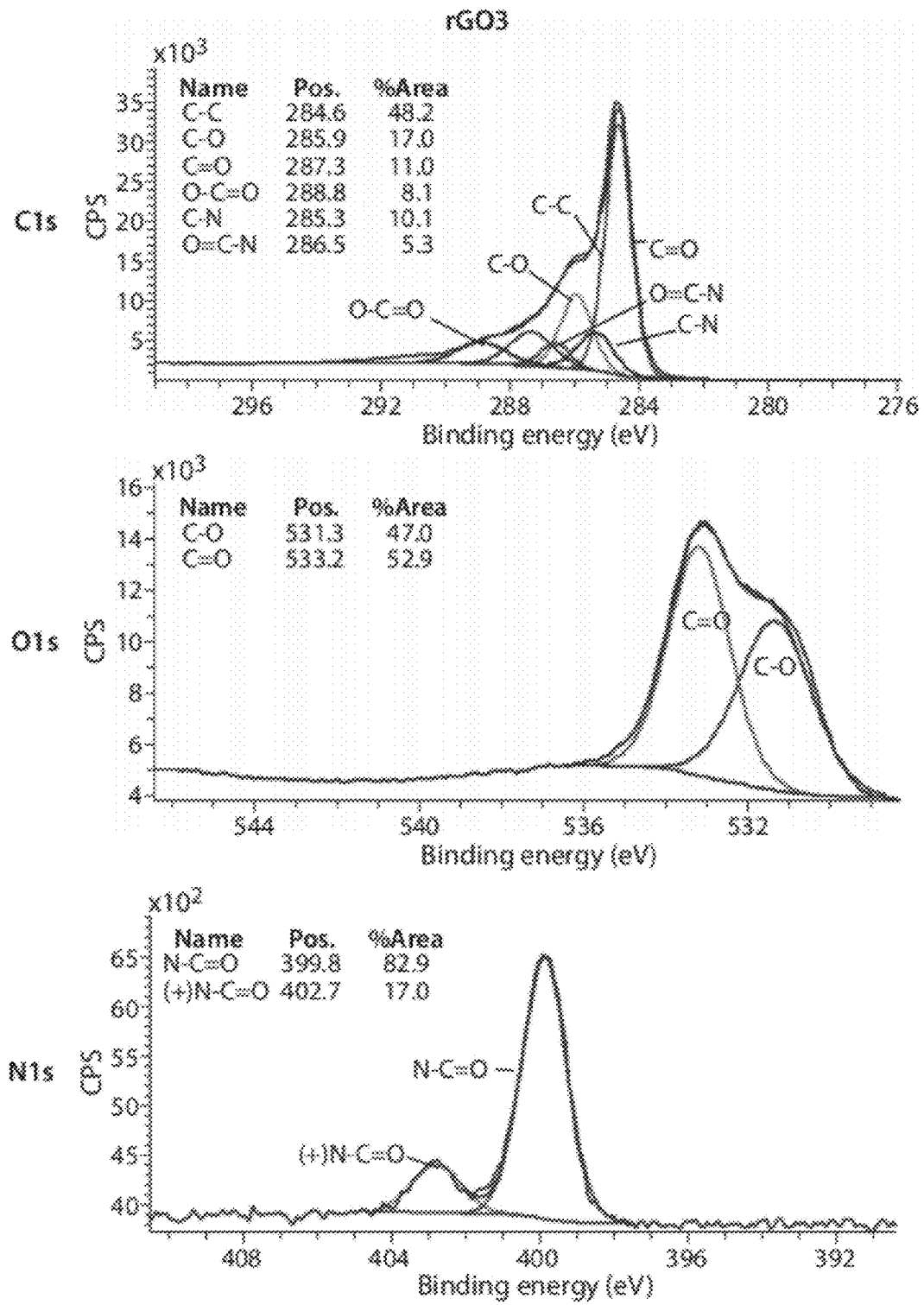

Incorporation of amide functionalities onto the surface of graphite oxide (to yield rearranged graphite oxide, rGO) has been investigated by a wide variety of techniques: XPS, TGA, FTIR, XRD. XPS is the most commonly used technique for quantative as well as qualitative characterization of elemental composition of carbon materials. By XPS both nitrogen incorporation as well as substantial deoxygenation of the samples was confirmed. FIG. 2 show the XPS data for A) rGO3c and B) rGO3. Graphite oxide (GO) and material from control reactions (rGO1c, rGO2c, rGO3c) exhibit only two signals in XPS survey analysis, corresponding to the C1s (around 285 eV) and O1s (around 532 eV) peaks. The carbon to oxygen (C/O) ratio calculated according to atomic % is 2.1, which is common for graphite oxides obtained by Hummer's method. All three rearranged graphite oxides (rGO1, rGO2, rGO3) show an additional band attributed to the N1s peak (around 400 eV) as shown by sample XPS spectra in FIG. 2 show. FIG. 3 shows hi-res XPS data of (from top) C1s, O1s and N1s regions of (A) GO and (B) rGO3. Elemental compositions of the samples (see Table 1) have been calculated. Nitrogen incorporation is higher with increasing reaction temperature.

Further work-up of the sample after reaction yields exfoliated material (rGO3b) with 3.7% nitrogen incorporation which corresponds to one —$CH_2$—$C(O)N(CH_3)_2$ group grafted on the surface of rGO per 18 C atoms (4-5 rings) of the rearranged graphite oxide sheet. Oxygen species content may be higher than in rGO3 because of epoxide opening basic conditions introducing more oxygen species onto the surface of rearranged graphene. In some cases, the reaction causes simultaneous deoxygenation of graphite oxide at levels comparable to chemical methods of reduction. Some degree of deoxygenation can also be noticed in control reactions but it is generally lower (see Table 1 for C/O ratio). After annealing at 500° C., the amount of nitrogen was considerably smaller, for example, due to cleavage of introduced groups, still accounting for 1 introduced group per 57 graphene carbons that is approximately 20 rings.

By analysis of hi-res XPS data a drop in C—O species content was noted in the rearranged material both on the basis of C1sd and O1s signals. In the C1s region new components can be found attributed to amide moieties. The nitrogen band is composed of two separate peaks that can be attributed to amide and most probably charged amide functionalities.

TABLE 1

Atomic percentage for the analyzed samples calculated from XPS data.

|  | C1s | O1s | N1s | C/O* |
|---|---|---|---|---|
| GO | 68.1 | 31.9 | — | 2.1 |
| rGO1 | 84.6 | 14.1 | 1.3 | 6.2 |
| rGO2 | 85.5 | 12.4 | 2.1 | 6.3 |
| rGO3 | 85.8 | 11.3 | 3.1 | 8.9 |
| rGO3b | 79.8 | 16.5 | 3.7 | 5.1 |
| rGO3b (500) | 85.7 | 12.9 | 1.4 | 7.0 |
| rGO1c | 74.0 | 26.0 | — | 4.0 |
| rGO2c | 75.5 | 24.5 | — | 3.0 |
| rGO3c | 80.1 | 19.9 | — | 4.0 |
| rGO3c | 80.1 | 19.9 | — | 4.0 |

*C and O atoms of graphene sheets (without C and O in incorporated functionalities)

Figure 4:
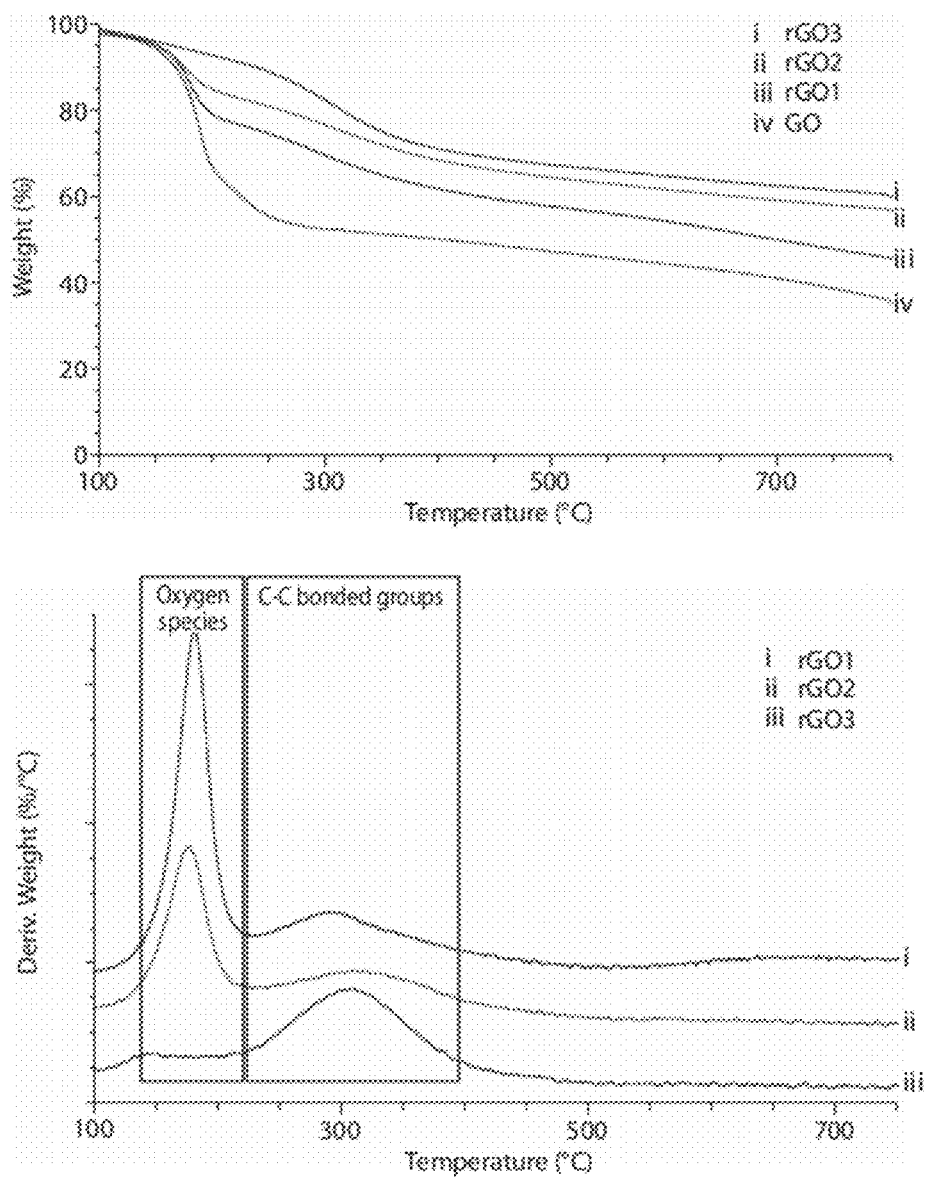
FIG. 4 shows TGA and dTGA spectra of materials, including materials of the present invention, according to some embodiments.

Deoxygenation of the material can be confirmed by TGA analysis. The TGA mass-loss curve of graphite oxide exhibits one mass loss region at around 150° C. that is usually attributed to oxygen species. After rearrangement a gradual diminishing of this slope was observed and appearance of new mass loss region spanning from 230 to 400° C. (see FIG. 4). Specifically, FIG. 4 shows (top) TGA and (bottom) dTGA (rate of mass loss) of the samples. As has been demonstrated previously, in this temperature range, one can observe loss of ligands bonded by C—C bonds to the reduced graphite sheet which may be occurring in this material. It is also conspicuous that the second slope is most pronounced for rGO3, which is the sample with highest level of functionalization (highest nitrogen incorporation as shown by XPS).

Figure 5:
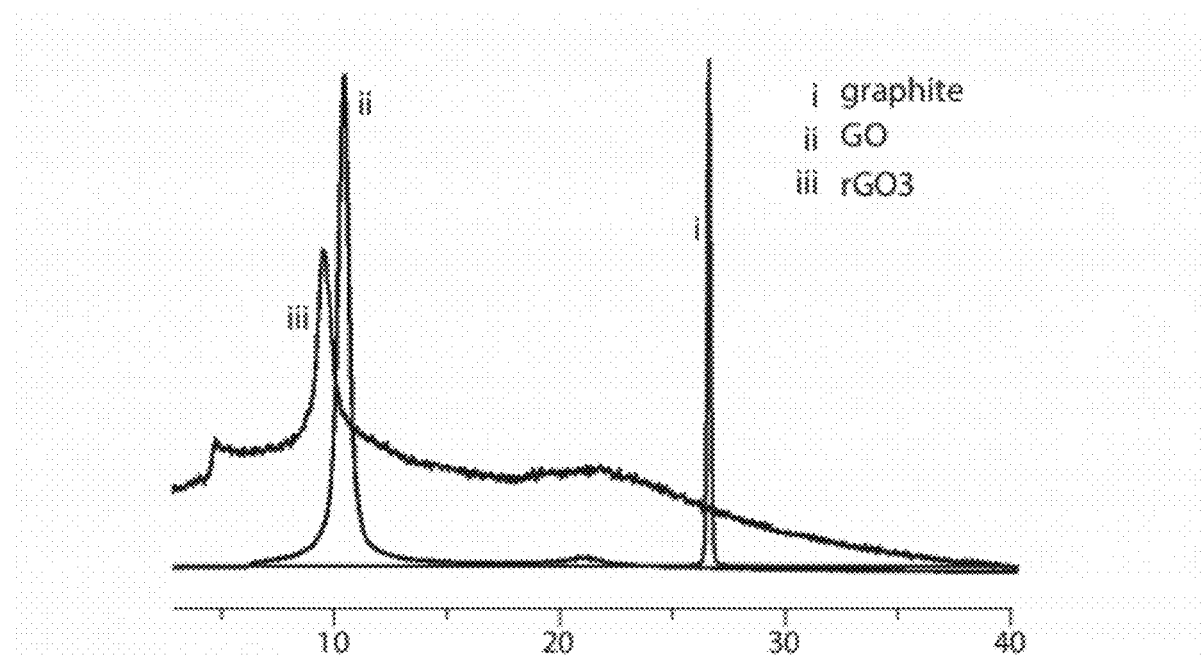
FIG. 5 shows XRD spectra of materials, including materials of the present invention, according to some embodiments.
Figure 6:
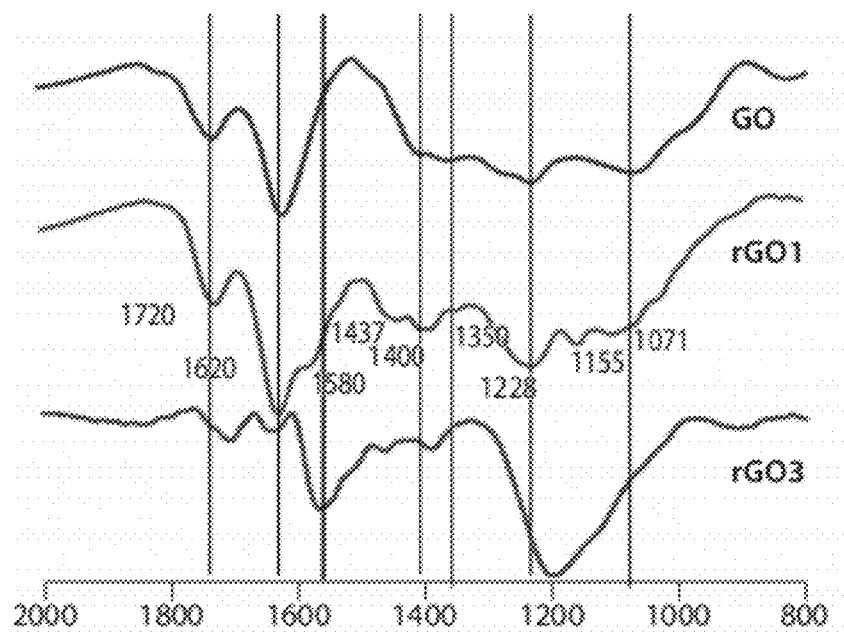
FIG. 6 shows FTIR spectra of materials, including materials of the present invention, according to some embodiments.

In x-ray diffraction experiments, GO exhibits a strong signal corresponding to the typical graphite oxide spacing of 8.4 Å (10.5 Θ). After rearrangement moderately strong signal appears at 9.3 Å (9.4 Θ). Larger spacing than in GO is caused by incorporation of longer substituents (—CH$_2$—C(O)N(CH$_3$)$_2$) on the reduced graphite oxide sheets in comparison to native groups (—O—, —OH). The spacing diminishes after annealing at 500° C. to 4.2 Å which corresponds to decomposition of introduced groups. Weak and broad signals at 4.2 Å for GO and rGO3 can be attributed to small domains of poorly exfoliated graphite regions or deoxygenated domains of graphite oxide. FIG. 5 shows XRD spectra of graphite, GO and rGO3 samples.

Figure 7:
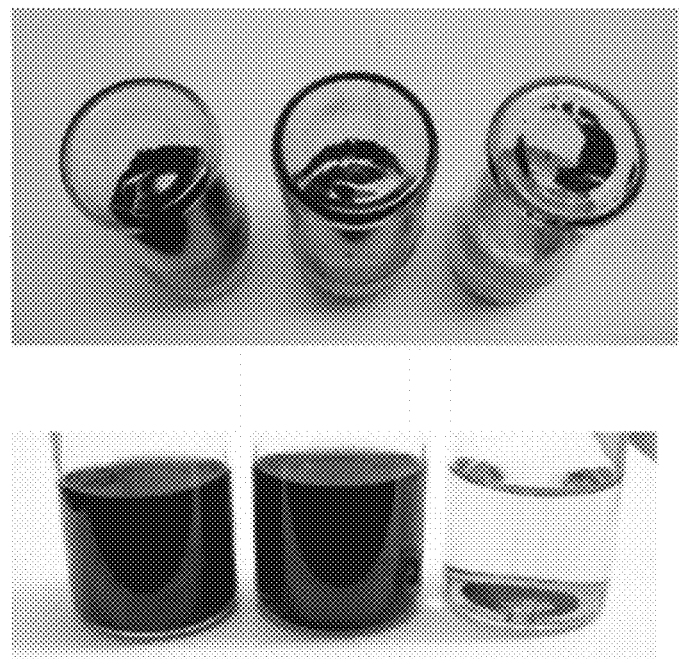
FIG. 7 shows solutions of materials of the present invention, according to some embodiments.

FTIR analysis of GO reveals a series of characteristic signals: 1726 cm$^{-1}$ C=O stretching vibrations from carbonyl and carboxyl groups, 1620 cm$^{-1}$ C=C stretching, skeletal vibrations from unoxidized graphitic domains, 1400 cm$^{-1}$ O—H bending vibrations, 1300-1350 cm$^{-1}$ C—OH stretching vibrations, 1200-1220 cm$^{-1}$ breathing vibrations from epoxy groups, 1060 cm$^{-1}$ v C—O. For rearranged samples a new signal at 1580 cm$^{-1}$ can be observed that can be attributed to C=C bonds being more pronounced after deoxygenation. The strong signal at 1200 cm$^{-1}$ for rGO3 indicates that epoxides are the main oxygen species in this material in contrast to the starting material (GO) which is in agreement with both XPS data as well as reaction mechanism. FIG. 5 shows baseline corrected FTIR spectra of GO, rGO1 and rGO3.

rGO3b material can be easily dispersed in various organic solvents: NMP, DMF, ACN, and DMSO. Highest stability of dispersions was noted for DMF (0.1 mg/mL) with no precipitation observed after 3 weeks. FIG. 7 shows rGO3 solutions in (from right) DMF, NMP and ACN at 0.1 mg/mL concentration after 3 weeks of sedimentation.

Example 3

Figure 11A:
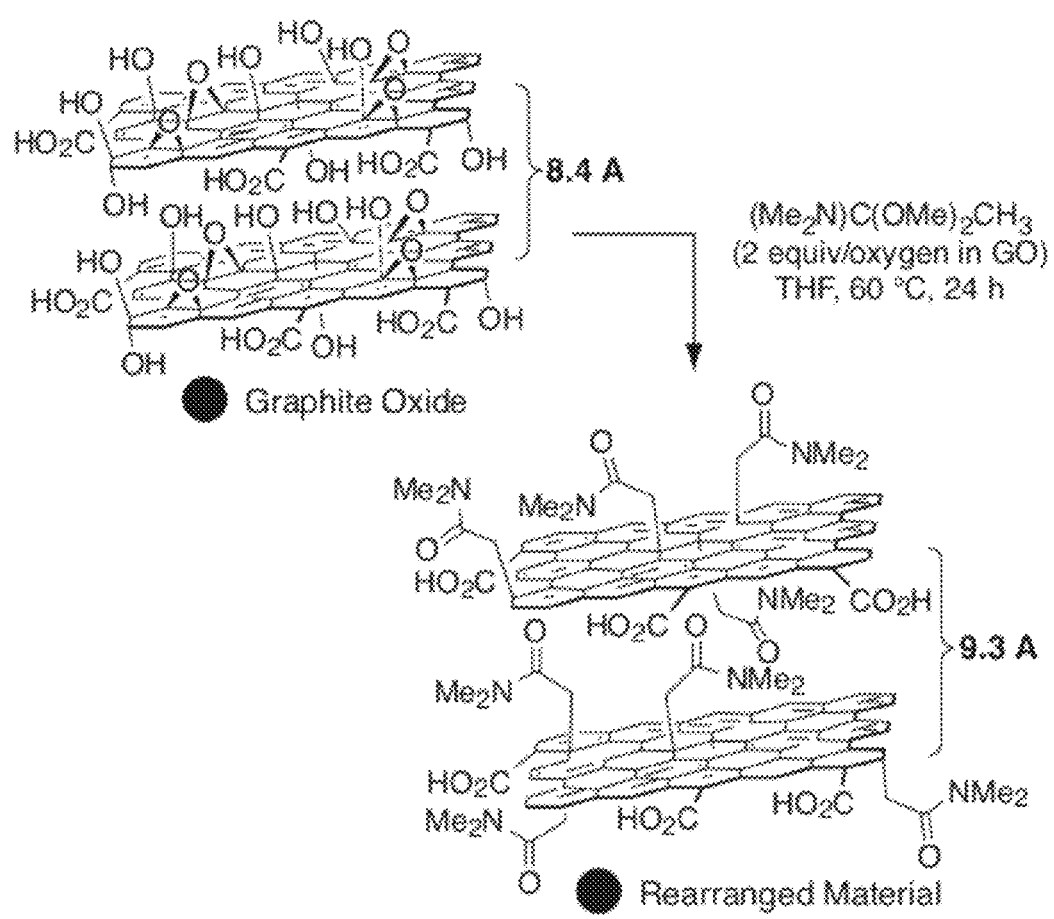
FIG. 11 shows (a) synthesis of allylic amide-functionalized graphene; (b) a space-filling model of the synthesis of allylic amide-functionalized graphene; (c) a photograph of a solution of graphene oxide and an aliquot taken 1 hour after the reaction of graphene oxide with $[(CH_3)_2N]C(OCH_3)_2CH_3$; (d) an FTIR spectrum of allylic amide-functionalized graphene oxide; (e) and X-ray diffraction plot for graphite, graphene oxide, and allylic amide-functionalized graphene oxide; (f) X-ray photoelectron spectroscopy (XPS) plots for graphene oxide, and allylic amide-functionalized graphene oxide; and (g) XPS data for graphene oxide, and allylic amide-functionalized graphene oxide.
Figure 11B:
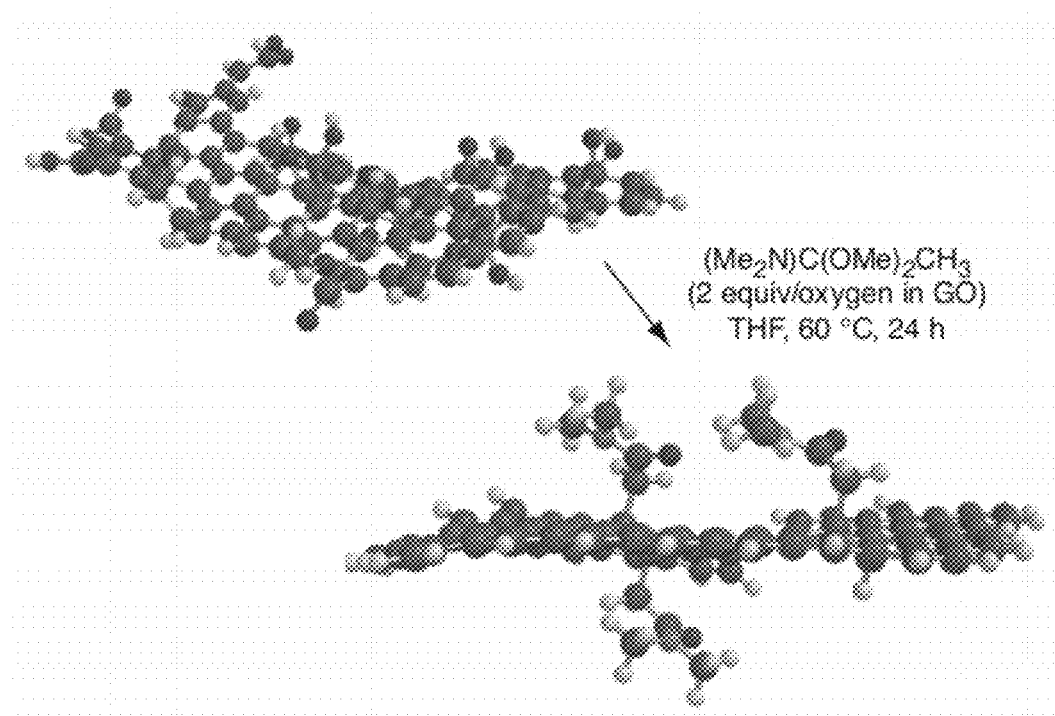
Figure 11C:
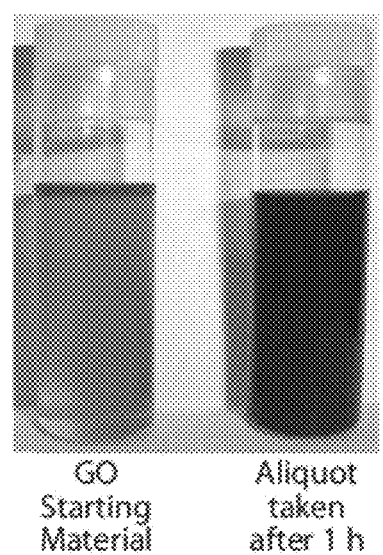
Figure 11D:
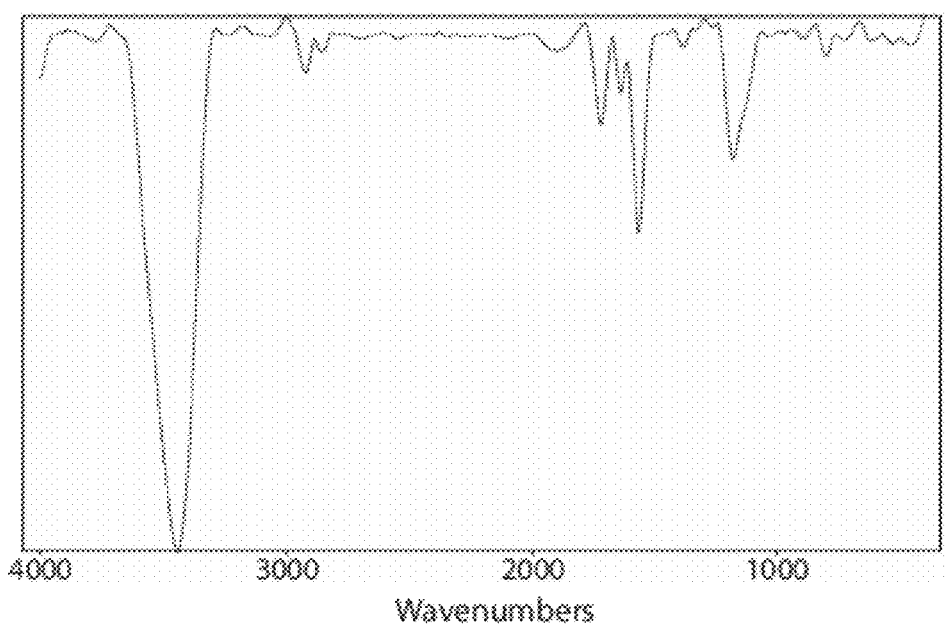
Figure 11E:
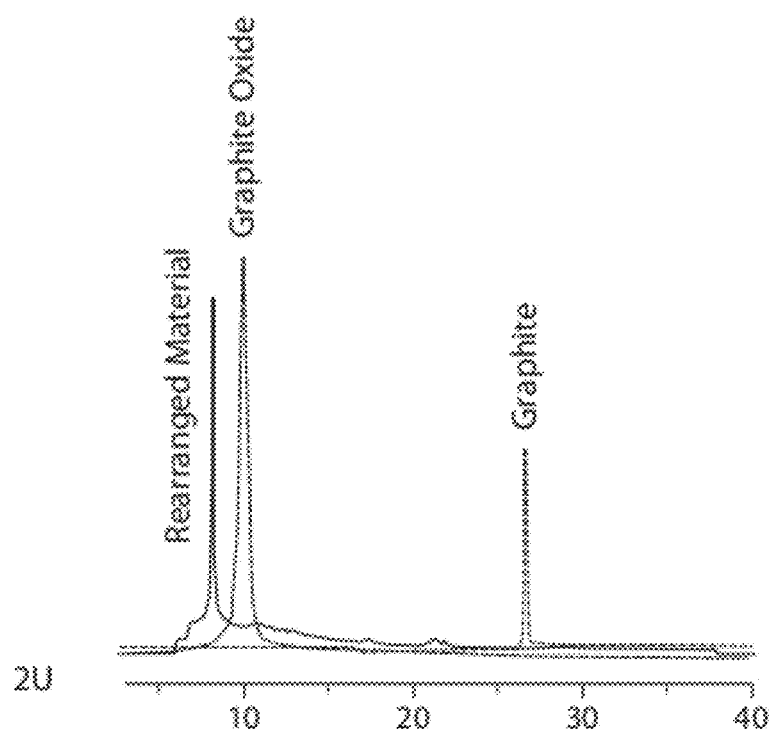
Figure 11F:
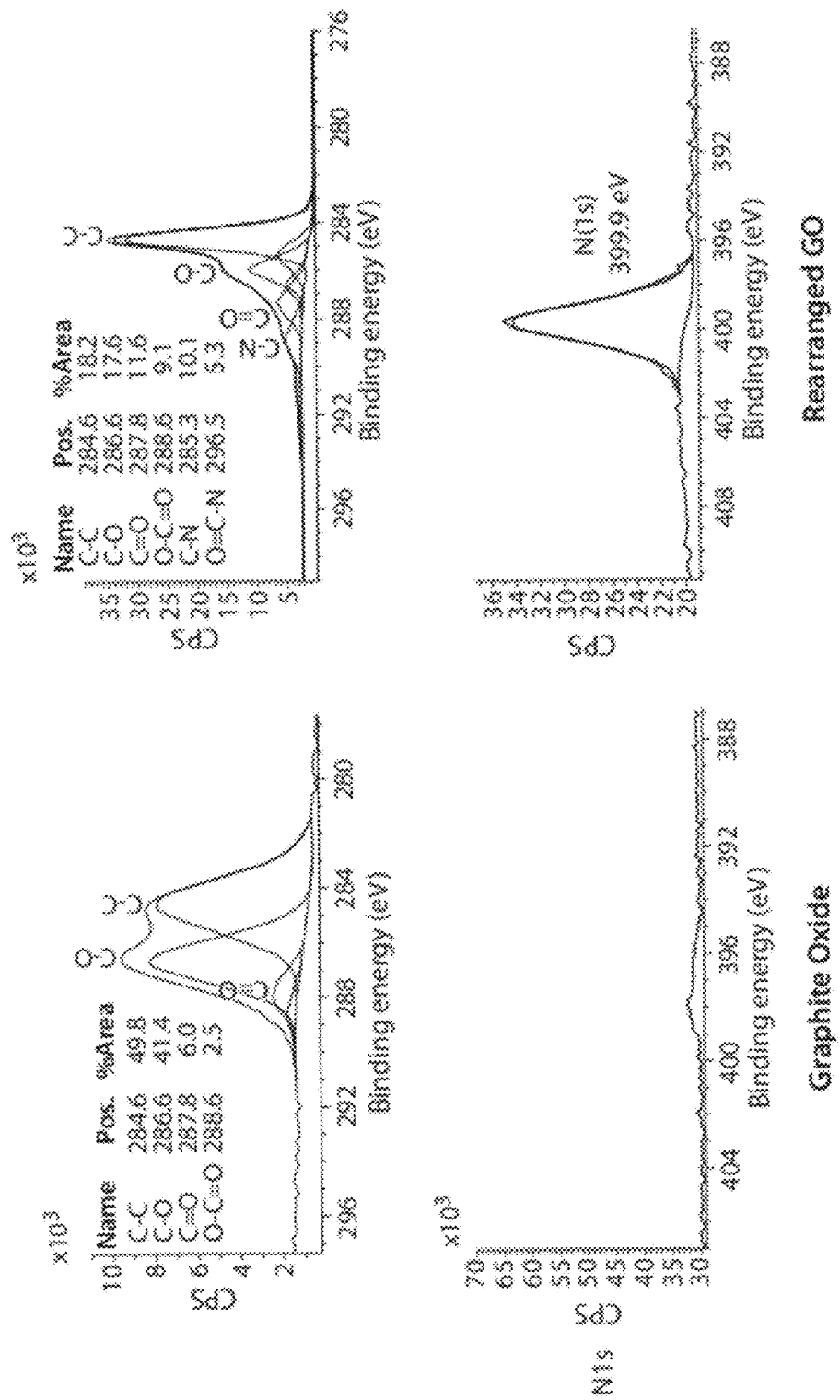

The following example describes the synthesis of allylic amide-functionalized graphene. (FIGS. 11A-B). As shown in FIG. 11C, after 1 hour of reacting graphene oxide with [(CH$_3$)$_2$N]C(OCH$_3$)$_2$CH$_3$, the solution turns black in color. Upon completion of the reaction, UV-vis data of the resulting material indicated re-establishment of a conjugated network, and an FTIR spectrum indicated the presence of amide groups by the appearance of amide C=O stretching bands. (FIG. 11D) XRD data for graphene, graphene oxide, and allylic amide-functionalized graphene oxide is shown in FIG. 11E. XPS plots for graphene oxide, and allylic amide-functionalized graphene oxide confirmed the presence of amide functionality on the graphene surface (dialkylamides on activated carbon=399/9 eV). (FIGS. 11F-G) Furthermore, TGA data indicated that the functionalization was covalent in nature and that by increasing the reaction temperature, C—O functionalization decreased and C—C functionalization increased.

Example 4

The following example describes saponification of modified graphene oxide. FIG. 12A shows reaction conditions used for the saponification of an allylic ester-functionalized graphene oxide. The XPS data shown in FIGS. 12B-C indicate that near-complete saponification of the dimethyl amide group occurred to give a graphene sheet covalently functionalized with allylic carboxylates.

Example 5

Figure 13A:
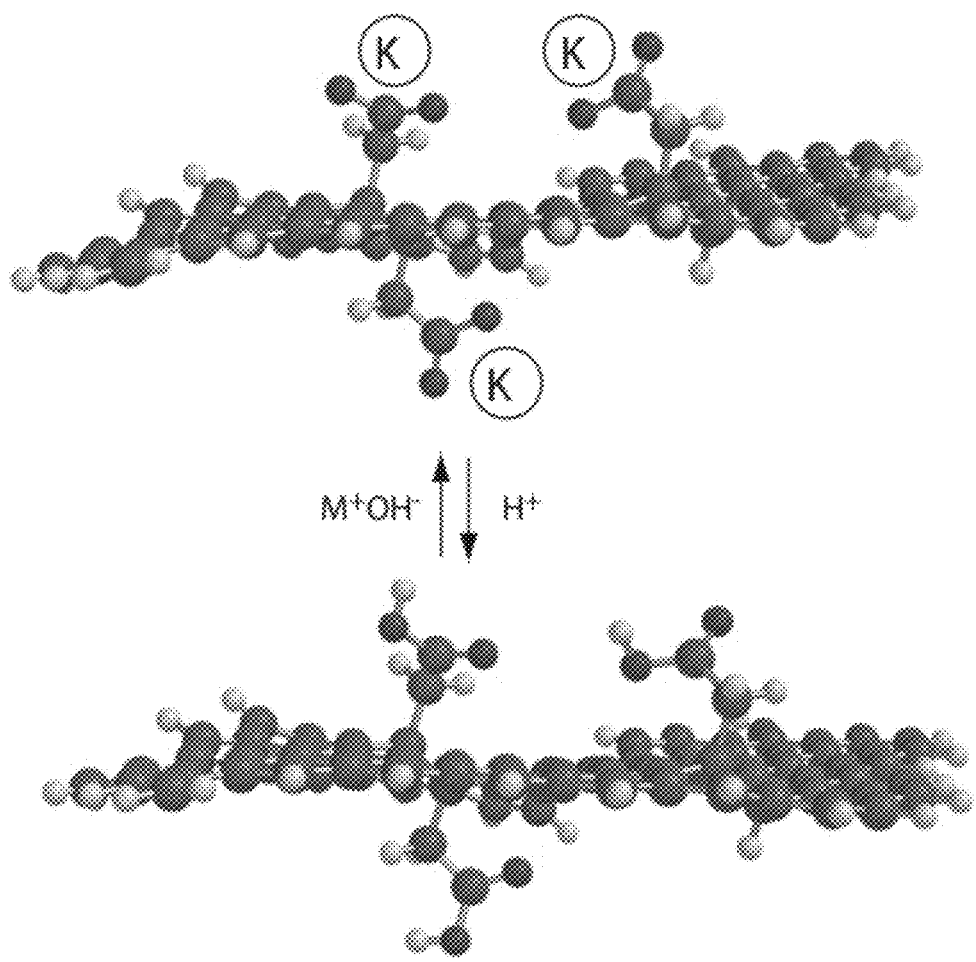
FIG. 13 shows (a) the reversible conversion of carboxylic acid-functionalized graphene oxide to a potassium salt carboxylate-functionalized graphene oxide; (b) the reversible formation of aqueous colloids containing potassium salt carboxylate-functionalized graphene oxide from carboxylic acid-functionalized graphene oxide; (c) a photograph of solutions of carboxylic acid-functionalized graphene oxide under various conditions; (d) zeta potential and conductivity data for carboxylic acid-functionalized graphene oxides.
Figure 13B:
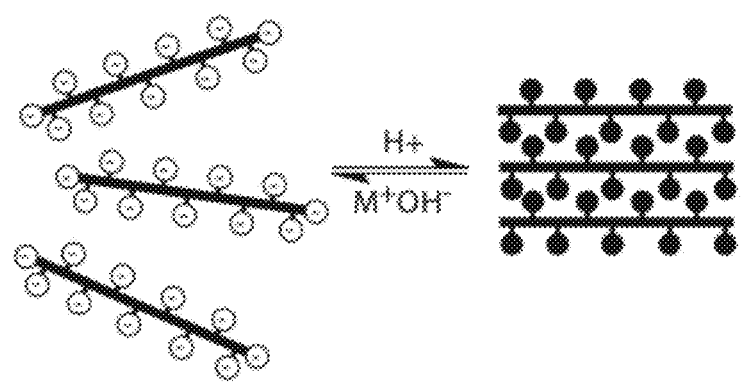
Figures 13C, 13D:
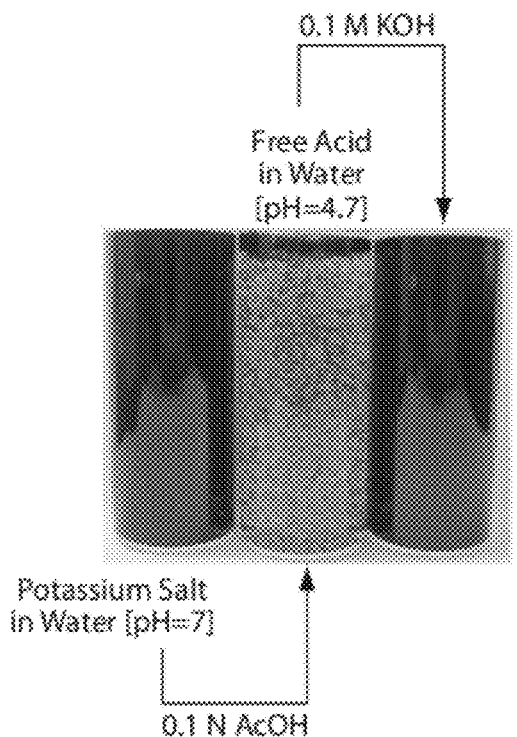

The following example describes the formation of stable graphene colloids using graphene substituted with allylic carboxylic acid groups. FIGS. 13A-B show the reversible conversion of carboxylic acid-functionalized graphene oxide to a potassium salt carboxylate-functionalized graphene oxide. As shown in FIG. 13C, the chemically converted graphene sheets can form stable aqueous colloids through electrostatic stabilization and can remain in solution without the need for polymeric or surfactant stabilizers. FIG. 13D shows the zeta potential and conductivity data for carboxylic acid-functionalized graphene oxides.

Example 6

Figure 14B:
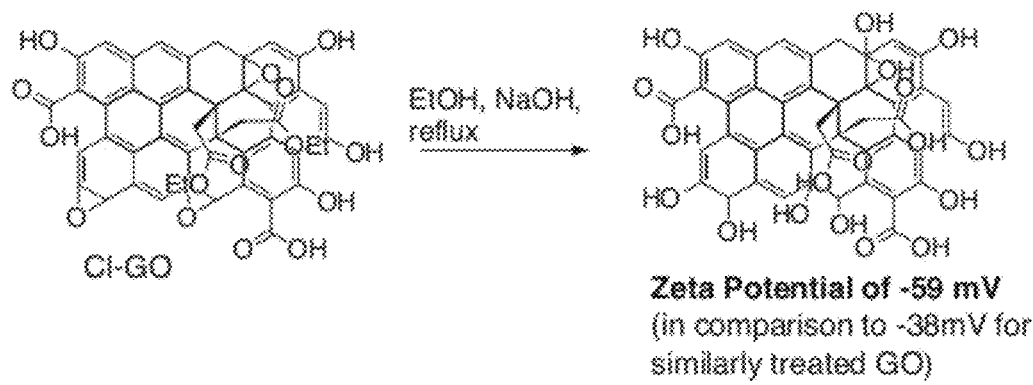
Figure 14C:
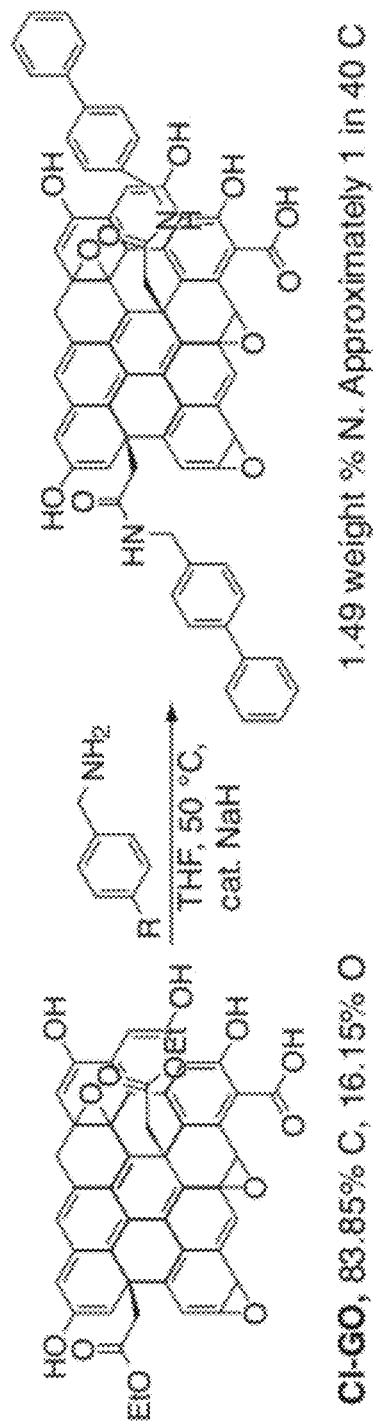
Figure 14D:
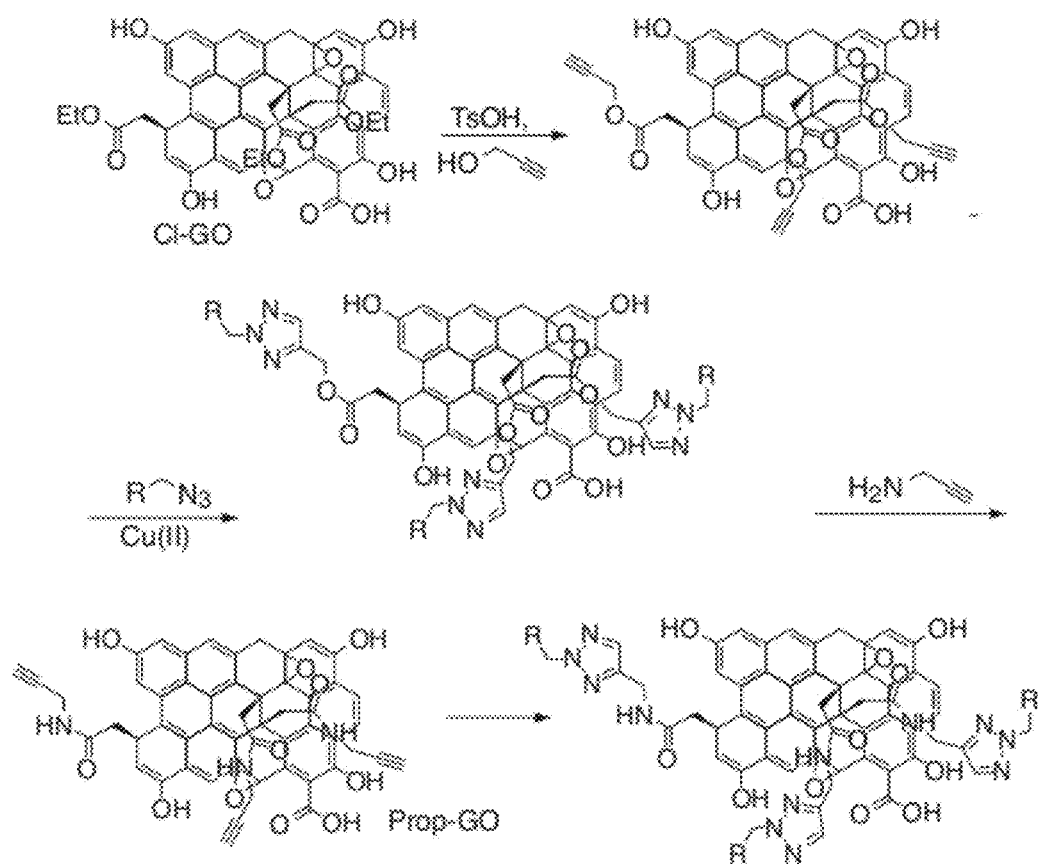
Figure 14E:
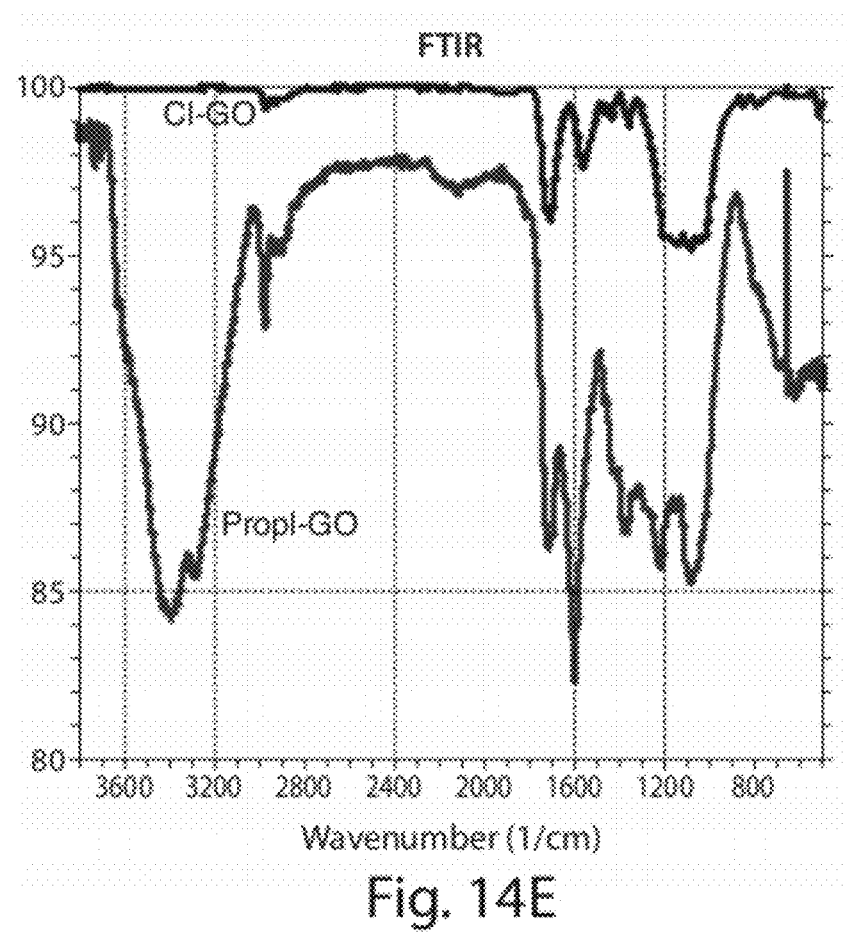
Figure 14F:
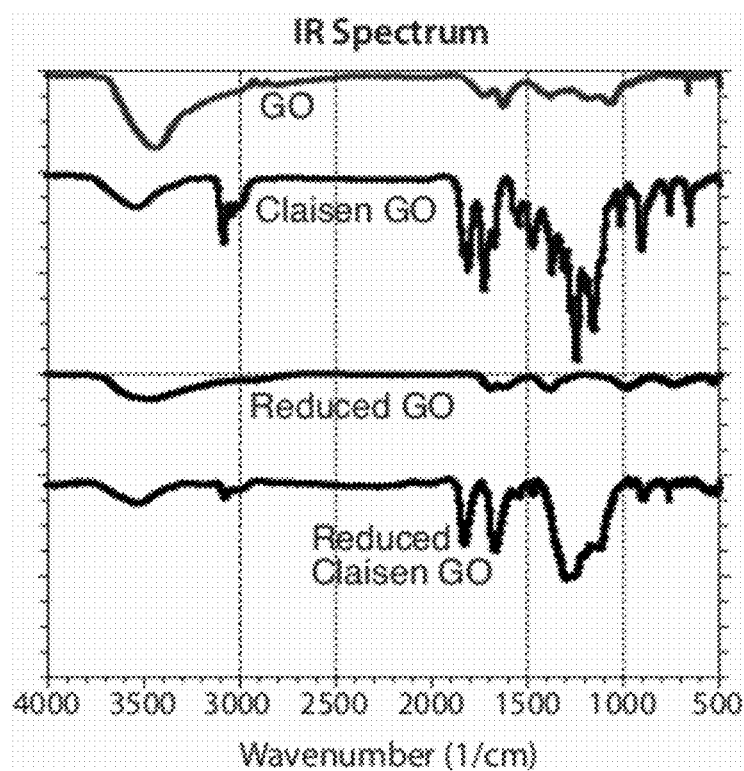
Figure 14G:
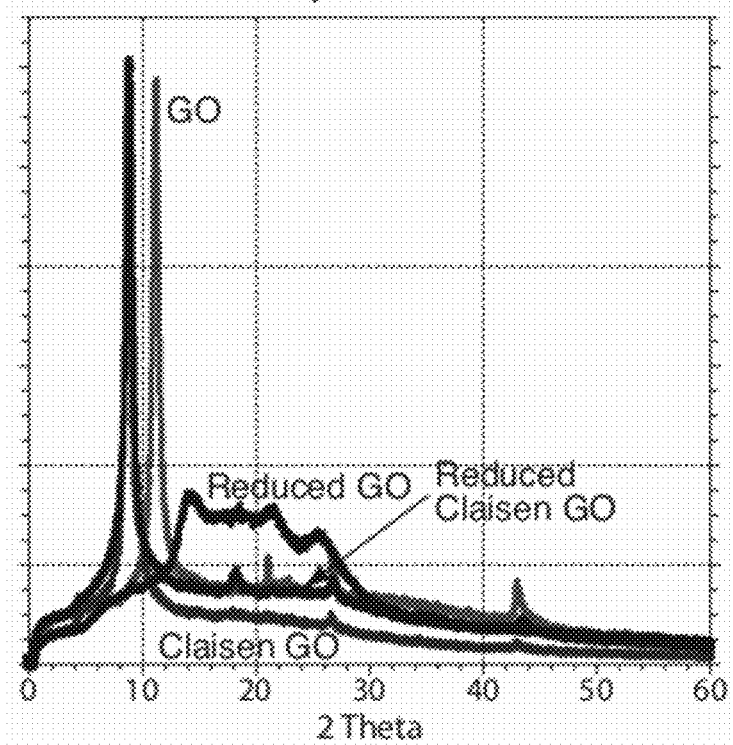

The following example describes the functionalization of graphene oxide via a Johnson Claisen reaction using CH$_3$C(OCH$_3$)$_3$ to create a vinyl-ether intermediate that rearranges to form an allylic ester, which can be further functionalized. (FIG. 14A) Examples of further functionalization of the allylic ester include saponification (FIG. 14B), transamidation (FIG. 14C), as well as the synthesis of an alkyne-containing group for use in click chemistry (FIG. 14D).

XRD was used to determine the distance between adjacent graphene sheets for various substituted graphene molecules, as shown in Table 2 below. Substitution on the basal plane of the graphene oxide sheets resulted in increased intersheet distance, relative to unsubstituted graphene sheets.

TABLE 2

Intersheet distance for various substituted graphene molecules.

| Material | Distance between two adjacent graphene sheets (Angstroms) |
|---|---|
| Graphene | 3.4 |
| Graphene Oxide | 8.49 |
| Reduced GO (via NaBH$_4$) | 5.5-3.4 (Adv. Func. Mater. 2009, 19, 1987.) |
| Claisen-GO (graphene oxide substituted on basal plane with allylic ethyl esters) | 9.93 |
| Reduced Claisen-GO (graphene oxide substituted on basal plane with allylic ethyl esters, upon being treated with a reducing agent) | 9.71 |
| Amide Claisen GO - (graphene oxide substituted on basal plane with allylic amides) | R = H, 10.45 A, R = Ph, 10.65 A |

Example 7

The following example describes the synthesis of functionalized graphene oxides via a Carroll rearrangement. (FIG. 15B) All glassware was flame-dried and the reactions were performed under nitrogen atmosphere using standard Schlenk techniques. Graphite powder was received from Alfa Aeser (natural, 325-mesh) and used without further purification. Graphite oxide was synthesized using a modified Hummer's method in which NaNO$_3$ is excluded.

Acylated Meldrum's acid was synthesized according to the following procedure.

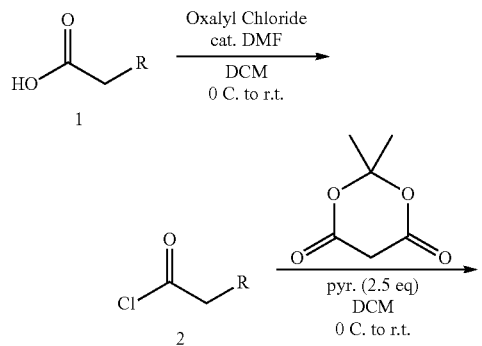

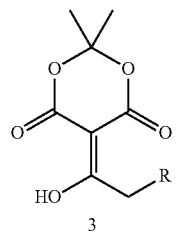

To form compound 2, 5.00 g (0.0218 mol) 3-(2-Bromophenyl)propanoic acid was dissolved in 50 mL dry methylene chloride and the resulting solution was stirred and brought to 0° C. with an ice-bath and 0.1 mL DMF added. 2.19 mL (3.19 g, 0.0251 mol, 1.15 eq) Freshly distilled oxalyl chloride was added by syringe over 10 min, and the ice-bath removed. The reaction vessel was sealed and vented through an oil bubbler to monitor the reaction progress. After 4 hrs, or when the reaction was no longer evolving gas, the solution was degassed with argon for 10 min to promote removal of residual HCl.

While this reaction was degassing, 3.61 g Meldrum's acid (0.0251 mol, 1.15 eq) was dissolved in 10 mL dry methylene chloride in a two-necked round bottom flask. The clear solution was stirred brought to 0° C. with an ice-bath and 4.41 mL (4.31 g, 0.0545 mol, 2.5 eq) dry pyridine was added by syringe over 5 min. To this solution, the solution containing compound 2 was added dropwise by cannula over 30 min. Upon addition the clear solution became an orange dispersion. After addition was complete, the reaction was stirred at 0° C. for 1 hr. Following this, the ice-bath was removed and the reaction stirred at room temperature for an hour. The now deep red dispersion was poured into a 50 mL solution of 2 M HCl containing ice. This mixture was then poured into a separatory funnel and the organic layer isolated. The organic layer was washed with 2×50 mL 2 M HCl and 1×50 mL brine, dried over MgSO$_4$ and filtered. The deep red solution was adsorbed onto 5 g silica gel and purified by column chromatography (eluent=9:1 hexanes:ethyl acetate, with 1% AcOH added) to produce 6.51 g (0.0183 mol, 84% yield) 5-(3-(2-bromophenyl)-1-hydroxypropylidene)-2,2-dimethyl-1,3-dioxane-4,6-dione (compound 3).

The synthesis of a functionalized graphene oxide is described below.

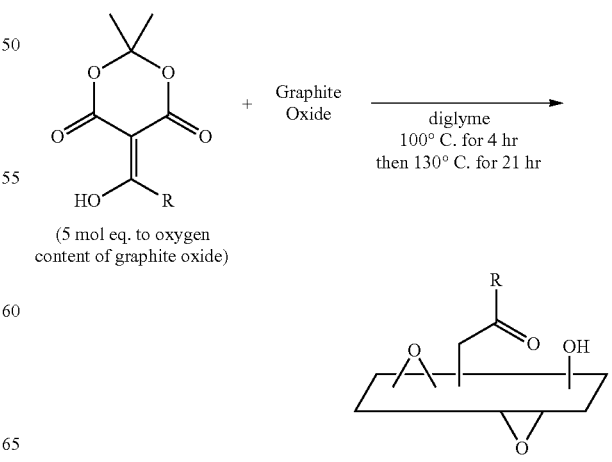

20 mg Graphite oxide was dispersed in 100 mL dry diglyme (diethylene glycol dimethyl ether). The dispersion was sonicated for 30 min and then 0.005 mol (5 eq. to oxygen content of graphite oxide) acylated Meldrum's acid was added. The dispersion was stirred for 1 hr at room temperature then immersed in a 100° C. oil bath. After approximately 10 min the previously brown dispersion turned black. After 4 hours, the oil bath temperature was increased to 130° C., and the reaction stirred for 21 hr. The black dispersion was filtered through a Millipore 0.4 µm PTFE membrane. The resulting filter cake was washed with a copious amount of acetone and then the black material was redispersed in 20 mL $CH_2Cl_2$. The dispersion was vortexed for 10 seconds then centrifuged at 11000 rpm for 10 min and the supernatant discarded. This procedure was repeated 3× with 20 mL $CH_2Cl_2$, followed by 2×20 mL acetone, 3×20 mL water, and 2×20 mL acetone. The resulting black slurry was then dried in a vacuum oven overnight at 50° C. to produce a fine black powder.

Alternatively, FIG. 15D shows another method for generating an acyl ketene. Heating 3-4 hours at 100 C, followed by 24 hours at 130 C.

Typically, two stages of heating were used, as graphite oxide often loses its oxygen functional groups upon heating and reduces back to graphene. To maximize the chances that the acyl ketene produced will attach to an allylic alcohol, a temperature of 100° C. for 4 hours is maintained to produce as many β-keto allyl esters on the surface of graphene as possible. The second stage of the transformation i.e., the Carroll rearrangement, is conducted at a relatively higher temperature.

Figure 16:
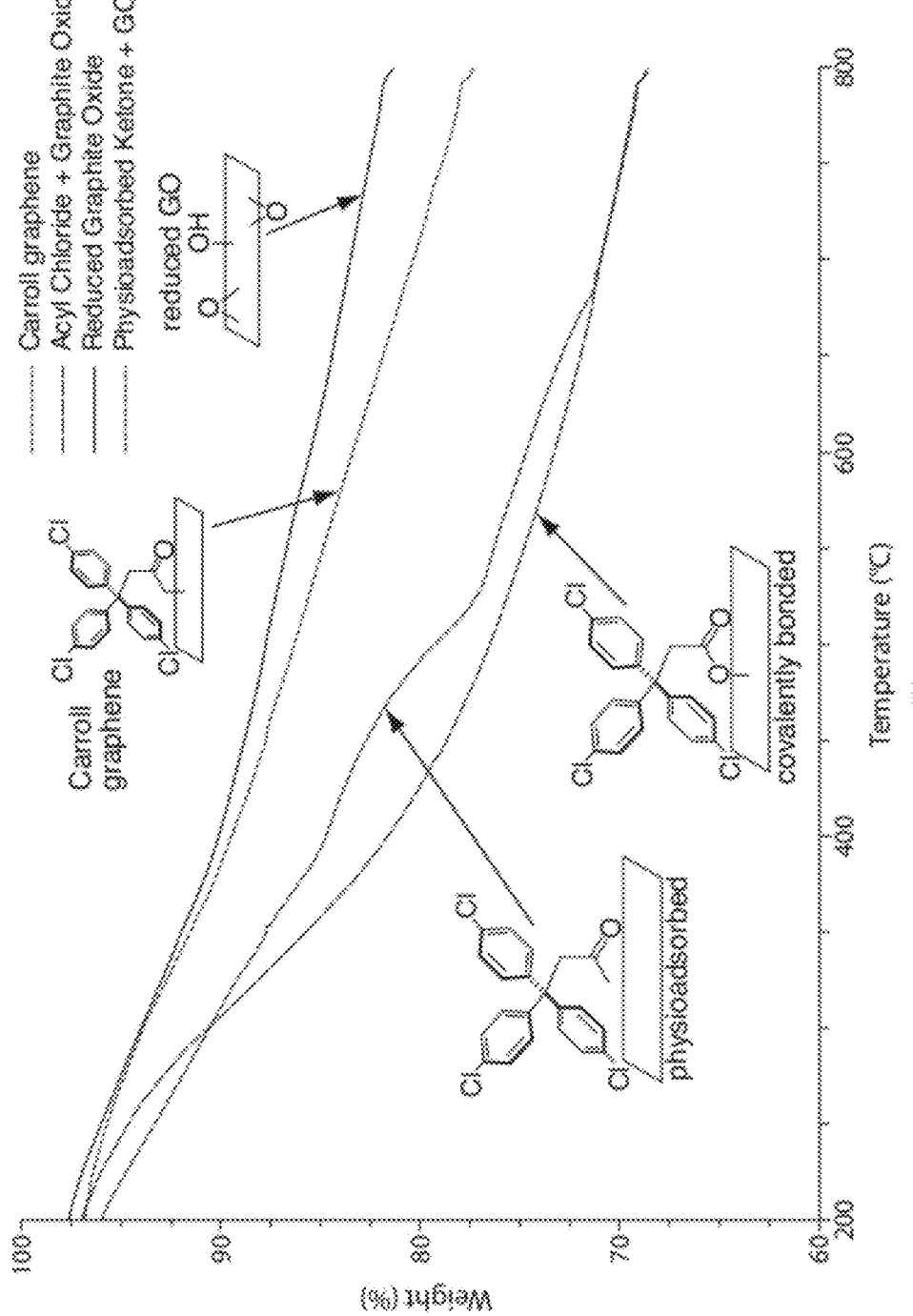
FIG. 16 shows thermogravimetric analysis data for various functionalized graphenes compared to unsubstituted graphene and unsubstituted graphene with physioadsorbed groups.

FIG. 16 shows thermogravimetric analysis data for various functionalized graphenes compared to unsubstituted graphene and unsubstituted graphene with physioadsorbed groups.

Figure 17:
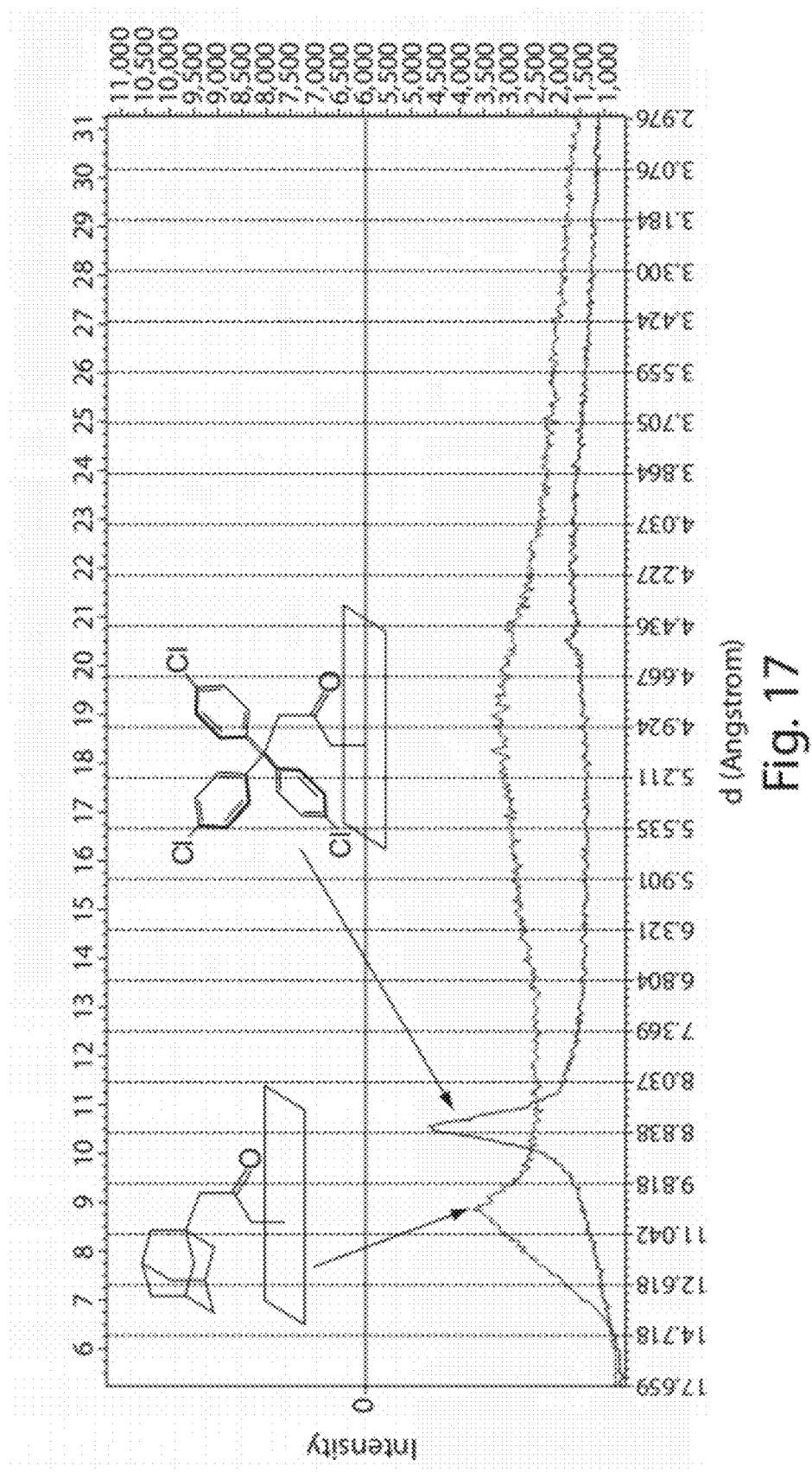
FIG. 17 shows X-ray diffraction data for graphene covalently functionalized on the basal plane.
Figure 18:
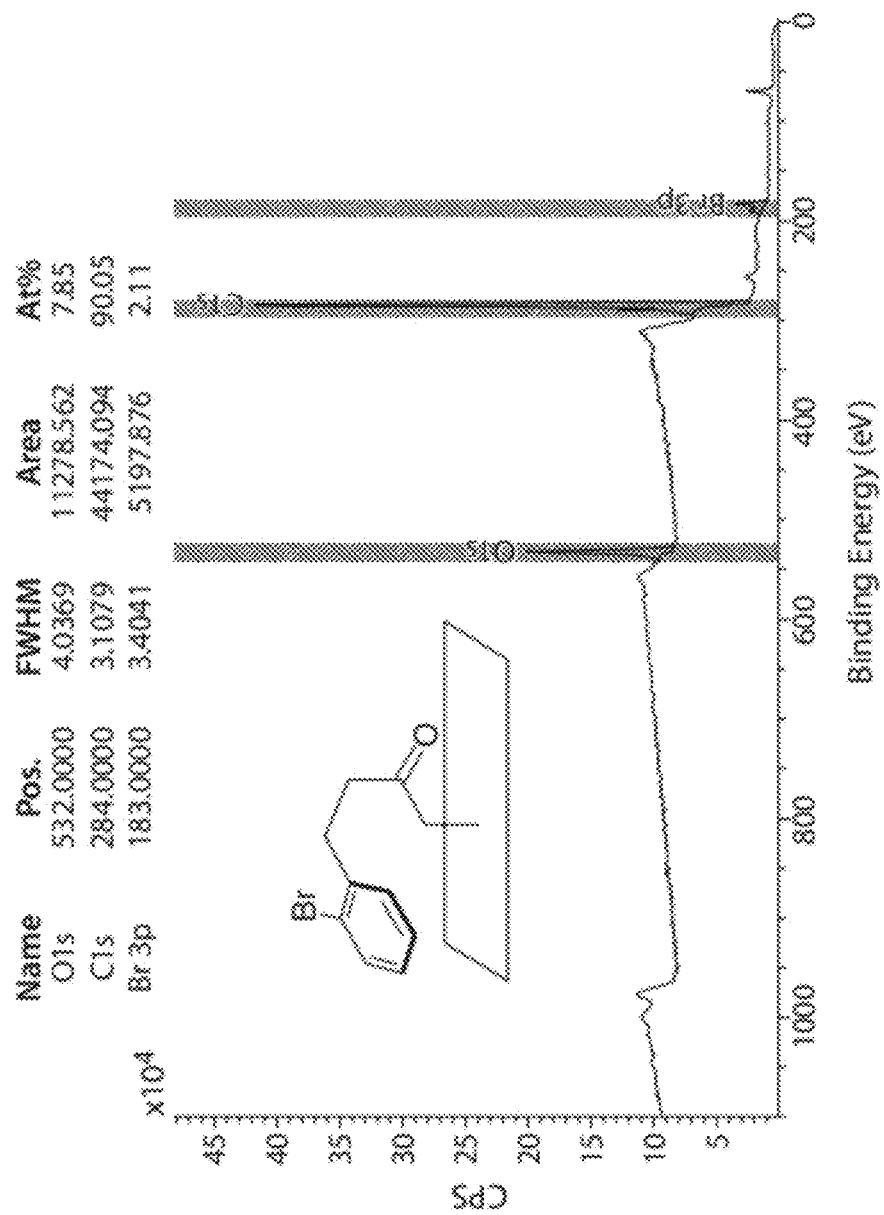
FIG. 18 shows XPS data for graphene covalently functionalized on the basal plane.

FIG. 17 shows X-ray diffraction data for graphene covalently functionalized on the basal plane, and FIG. 18 shows XPS data for graphene covalently functionalized on the basal plane. Based on this data, the functionalization was shown to occur many times across the basal plane of the graphene sheet, approximately once for every 20 carbon rings. The R-groups on the basal plane created a regular lattice with increased D-spacings relative to reduced graphite and reduced graphite oxide (3.3, 3.45 Å, respectively). XPS data also indicated that graphenes with heteroatoms (e.g., Br, Cl) include ~1 functionalization per 120 carbon atoms of graphene.

Figure 19:
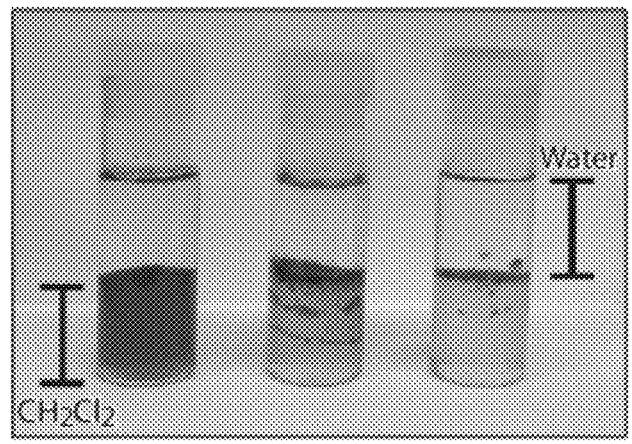
FIG. 19 shows a photograph of various samples containing covalently functionalized graphene, graphene with physioadsorbed groups, and unsubstituted graphene.
Figure 19:
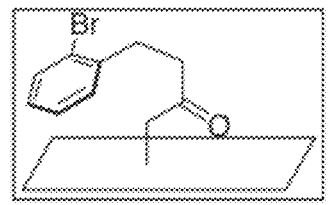
Figure 19:
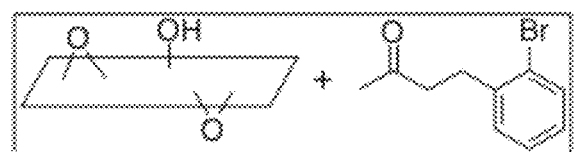
Figure 19:
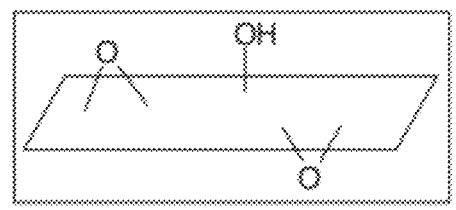

Additionally, it was found that functionalized graphenes can be used to crease stable dispersions. FIG. 19 shows a photograph of various samples containing covalently functionalized graphene, graphene with physioadsorbed groups, and unsubstituted graphene. It was observed that groups attached to graphene via non-covalent, physioadsorption did not impart the same kind of dispersablility as group that are attached to the basal plane of graphene covalently.

While several embodiments described herein have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings described herein is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition, comprising:
graphene or graphene oxide comprising at least one functional group associated with the graphene or graphene oxide, wherein the at least one functional group has the structure:

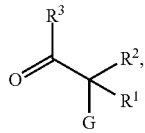

wherein $R^1$, $R^2$, and $R^3$ are the same or different and each is independently a substituent, optionally substituted; and
G comprises a carbon atom of the graphene or graphene oxide.

2. The composition of claim 1, wherein:
$R^1$ and $R^2$ are the same or different and each is independently hydrogen, alkyl, heteroalkyl, cycloalkyl, alkenyl, or aryl, any of which is optionally substituted.

3. The composition of claim 1, wherein:
$R^3$ is hydrogen, alkyl, aryl, alkenyl, cycloalkyl, heteroalkyl, heteroaryl, $N(R^4)_2$, $SR^4$, $Si(R^4)_2$, $OR^4$, or OM, any of which is optionally substituted,
M is a metal or cationic species; and
each $R^4$ is independently a substituent, optionally substituted.

4. The composition of claim 1, wherein the functional group comprises an electrochemically active species.

5. The composition of claim 4, wherein the electrochemically active species is a conducting polymer, metal, semimetal, or semiconductors.

6. The composition of claim 1, wherein the functional group is capable of reducing oxygen.

7. The composition of claim 1, wherein the functional group comprises a ligand for binding one or more metal atoms.

8. The composition of claim 1, wherein the functional group is capable of associating with and/or storing redox active species.

9. The composition of claim 8, wherein the redox species is lithium.

10. A method for fabricating a functionalized carbon-based nanostructure, comprising:
providing a carbon-based nanostructure comprising a first allylic functional group;
reacting the carbon-based nanostructure with a reactant comprising at least one carbon atom to transform the first allylic functional group into a second allylic functional group; and
allowing the second allylic functional group to undergo a rearrangement via a sigmatropic rearrangement reaction,
thereby forming a carbon-carbon bond between the at least one carbon atom within the reactant and a carbon atom within the carbon-based nanostructure,
wherein the carbon-based nanostructure is graphene or graphene oxide.

11. The method of claim 10, wherein the reactant comprising at least one carbon atom is $CH_3C(OCH_3)_3$.

12. The method of claim 10, wherein the reactant comprising at least one carbon atom is an acyl ketene species.

13. The method of claim 10, wherein the first allylic functional group is positioned on or within the basal plane of the graphene or graphene oxide.

14. The method of claim 10, further comprising:
treating the carbon-based nanostructure with a reducing agent.

15. A method for fabricating a functionalized carbon-based nanostructure, comprising:
providing a carbon-based nanostructure including a group having the formula (I):

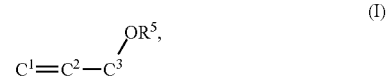

wherein $C^1$, $C^2$, and $C^3$ are part of a fused network of aromatic rings within the carbon-based nanostructure and $OR^5$ is a pendant group of the fused network of aromatic rings, and $R^5$ is a substituent, optionally substituted; and
reacting the carbon-based nanostructure with a reactant to produce a group having the formula (II):

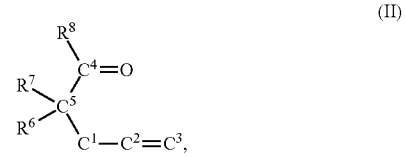

wherein $R^6$, $R^7$, and $R^8$ are the same or different and each is independently a substituent, optionally substituted.

16. The method of claim 15, wherein the reacting proceeds via an intermediate group having formula (III):

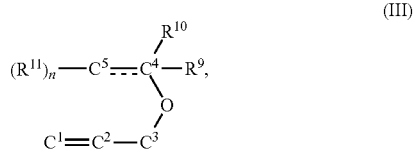

wherein $R^9$, $R^{10}$, and $R^{11}$ are the same or different and each is independently a substituent, optionally substituted;
or wherein $R^9$ and $R^{10}$ together form $=NR^{14}$ or $=O$;
$R^{14}$ is a substituent, optionally substituted;
n is 2 or 3; and
===== represents a single or double bond.

17. The method of claim 16, wherein the group of formula (III) comprises the structure:
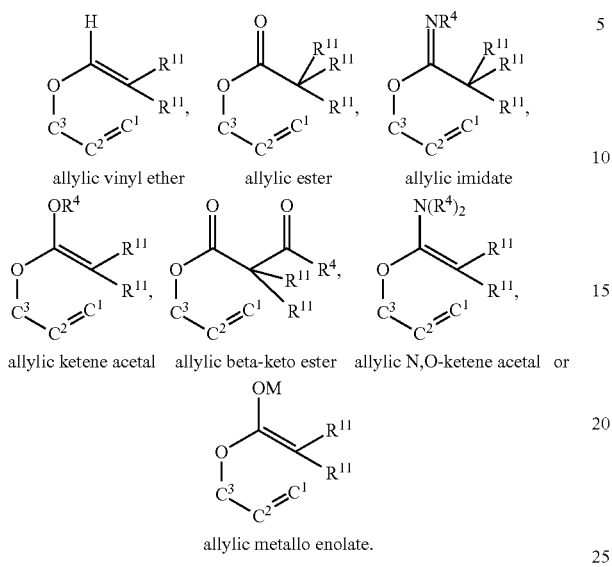
allylic vinyl ether    allylic ester    allylic imidate
allylic ketene acetal    allylic beta-keto ester    allylic N,O-ketene acetal  or
allylic metallo enolate.
* * * * *